(12) United States Patent
Araujo

(10) Patent No.: US 11,406,364 B2
(45) Date of Patent: Aug. 9, 2022

(54) SELECTIVELY EXTENDABLE AND RETRACTABLE BIOPSY DEVICES

(71) Applicant: Cyrillo Araujo, Madison, MS (US)

(72) Inventor: Cyrillo Araujo, Madison, MS (US)

(73) Assignee: Access Health, LLC, Tampa, FL (US)

( * ) Notice: Subject to any disclaimer, the term of this patent is extended or adjusted under 35 U.S.C. 154(b) by 449 days.

(21) Appl. No.: 15/912,863

(22) Filed: Mar. 6, 2018

(65) Prior Publication Data

US 2018/0256138 A1 Sep. 13, 2018

Related U.S. Application Data

(60) Provisional application No. 62/468,811, filed on Mar. 8, 2017.

(51) Int. Cl.
*A61B 10/02* (2006.01)
*A61B 10/04* (2006.01)

(52) U.S. Cl.
CPC .. *A61B 10/0266* (2013.01); *A61B 2010/0208* (2013.01); *A61B 2010/045* (2013.01)

(58) Field of Classification Search
CPC .......... A61B 10/0266; A61B 2010/045; A61B 2010/0208
See application file for complete search history.

(56) References Cited

U.S. PATENT DOCUMENTS

| | | |
|---|---|---|
| 4,157,709 A | 6/1979 | Schuster et al. |
| 4,784,158 A | 11/1988 | Okimoto |
| 5,591,189 A | 1/1997 | Toon |
| 6,086,543 A * | 7/2000 | Anderson .......... A61B 10/0233 600/567 |
| 8,012,100 B2 | 9/2011 | Ward |
| 2002/0120211 A1 | 8/2002 | Wardle et al. |
| 2003/0225411 A1* | 12/2003 | Miller ................ A61B 17/3472 606/80 |
| 2005/0251063 A1* | 11/2005 | Basude .............. A61B 10/0266 600/564 |

(Continued)

FOREIGN PATENT DOCUMENTS

WO 2016182043 11/2016

OTHER PUBLICATIONS

PCTUS2018021368 International Search Report, dated May 11, 2018.

*Primary Examiner* — Devin B Henson
*Assistant Examiner* — Joseph A Tombers
(74) *Attorney, Agent, or Firm* — Workman Nydegger

(57) ABSTRACT

An exemplary biopsy device includes (i) an elongated body, (ii) a hollow needle coupled to the distal end of the elongated body, the hollow needle having a channel that spans the length of the hollow needle, (iii) a trigger associated with the elongated body, (iv) a stylet having or associated with a biopsy element, the stylet being disposed within the channel of the hollow needle, operably connected to the trigger, and configured to extend beyond the distal end of the hollow needle and subsequently retract within the channel of the hollow needle, and (v) a spring mechanism operably connected to the trigger such that the spring mechanism compresses in response to operation of the trigger, extending the biopsy element, and is configured to rebound following compression, the rebound causing the biopsy element to retract toward or within the hollow needle.

15 Claims, 10 Drawing Sheets

(56) References Cited

U.S. PATENT DOCUMENTS

| | | | |
|---|---|---|---|
| 2008/0269638 A1* | 10/2008 | Cooke | A61B 10/0275 600/567 |
| 2008/0281226 A1* | 11/2008 | Peters | A61B 10/0275 600/567 |
| 2009/0326412 A1* | 12/2009 | Pakter | A61B 10/0266 600/567 |
| 2011/0190660 A1* | 8/2011 | Levy | A61B 10/0275 600/566 |
| 2014/0018725 A1 | 1/2014 | Potter et al. | |
| 2016/0287437 A1 | 10/2016 | Evans et al. | |
| 2016/0354065 A1 | 12/2016 | Grillo Fernandez et al. | |

* cited by examiner

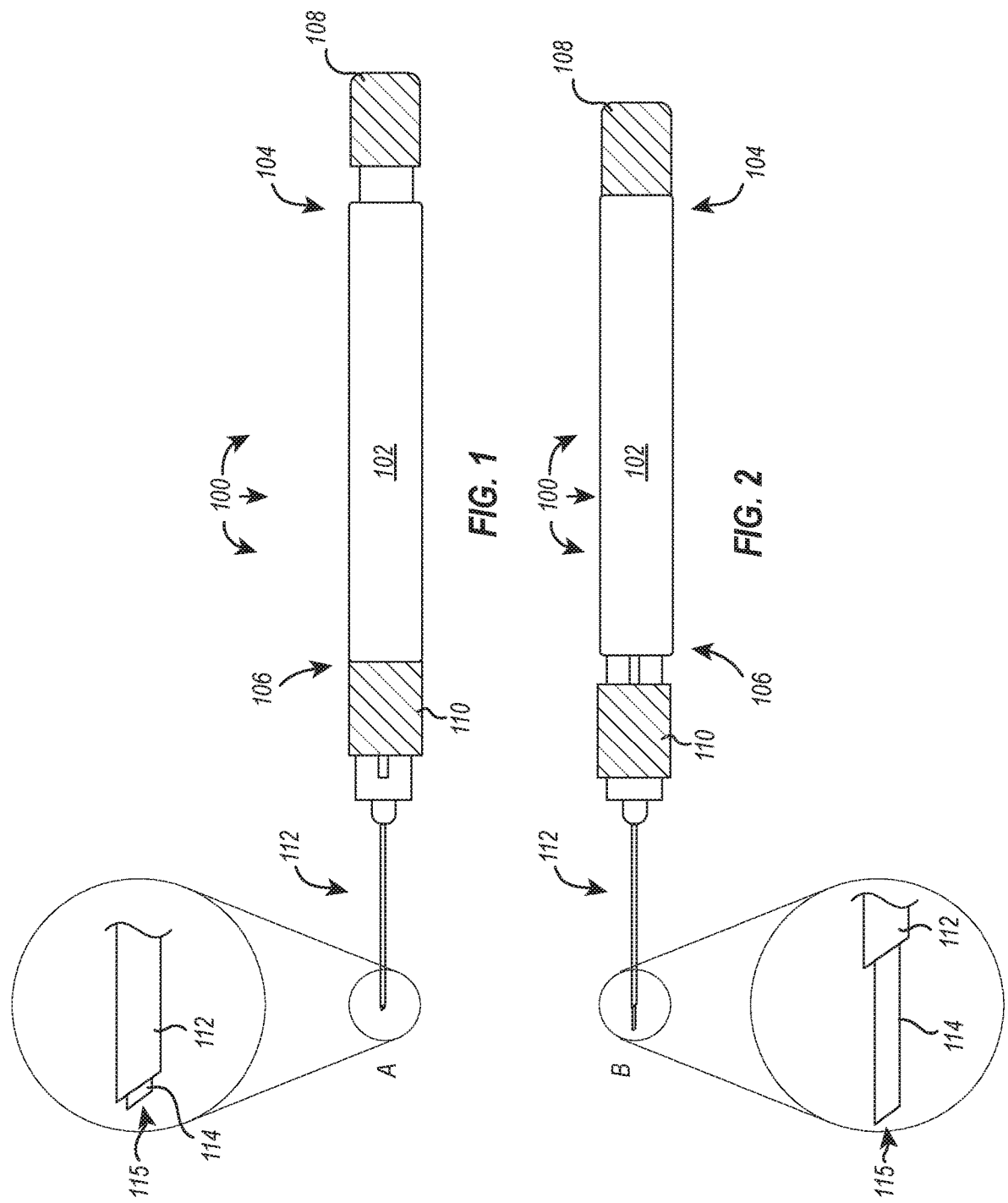

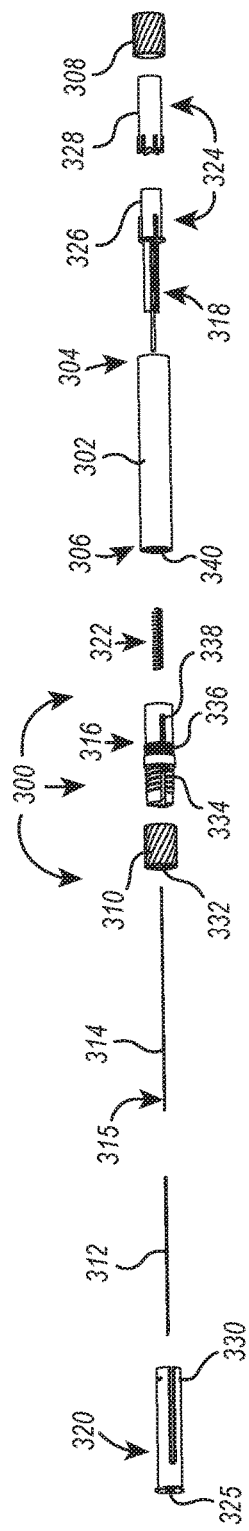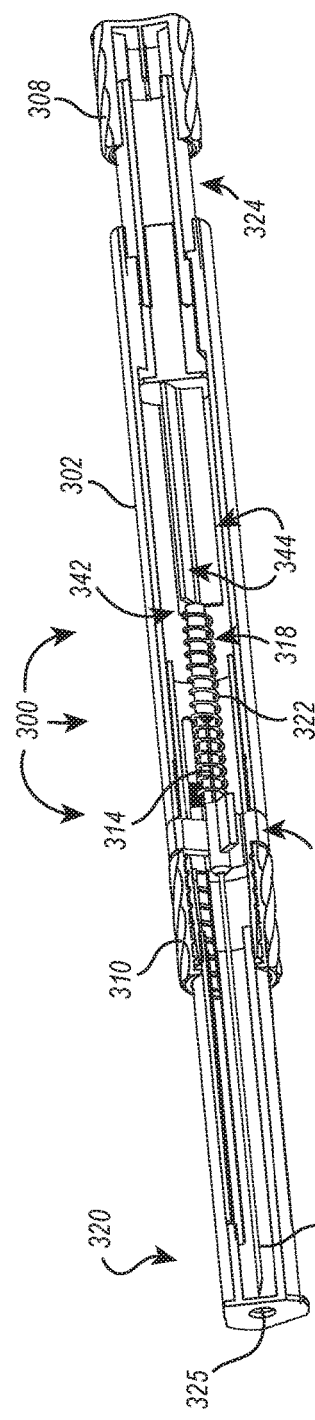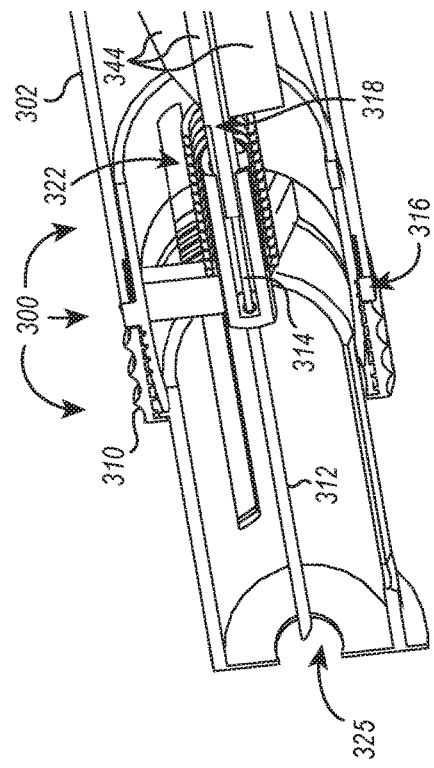

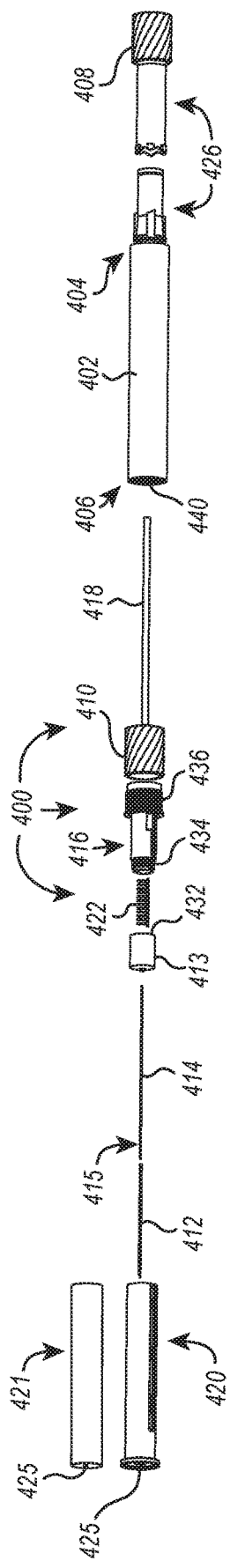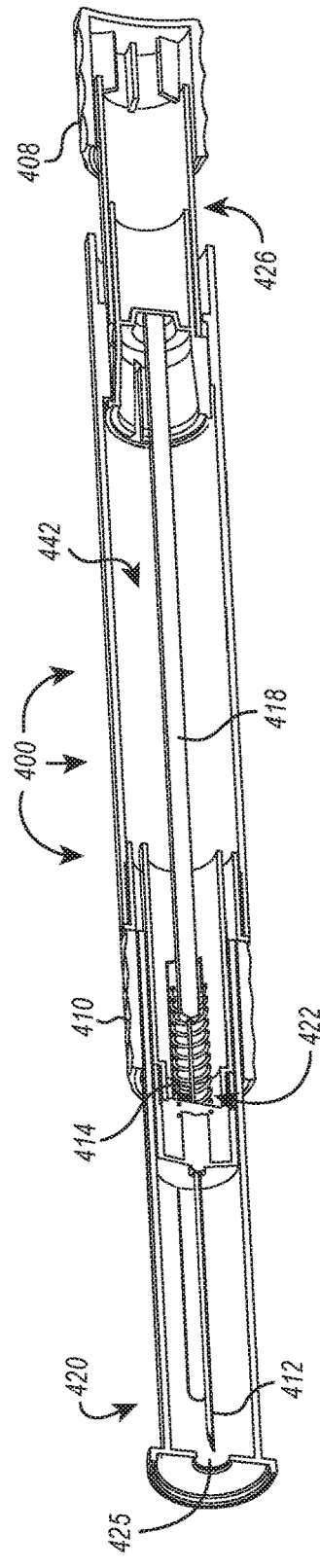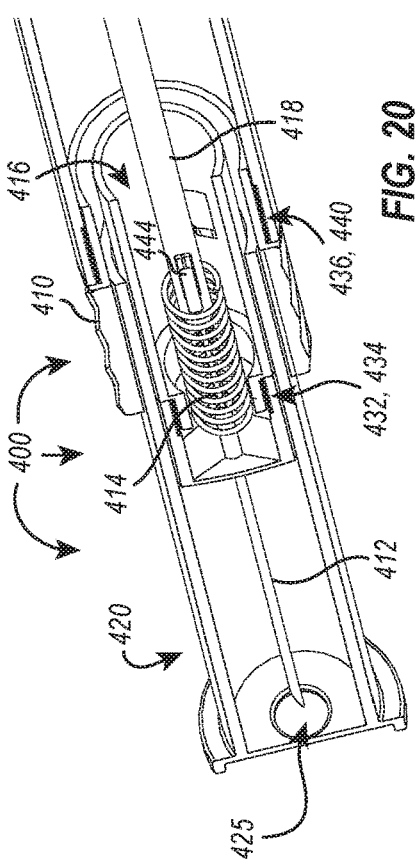

SELECTIVELY EXTENDABLE AND RETRACTABLE BIOPSY DEVICES

CROSS REFERENCES TO RELATED APPLICATIONS

This application claims the benefit of and priority to United States Provisional Patent Application No. 62/468,811 filed on Mar. 8, 2017, and entitled "EXTENDABLE AND RETRACTABLE BIOPSY DEVICES", which application is incorporated herein by reference in its entirety.

BACKGROUND

Technical Field

This disclosure generally relates to biopsy devices. More specifically, the present disclosure relates to biopsy devices that selectively extend and retract a biopsy element for obtaining a biopsy sample.

Related Technology

A biopsy is a procedure to remove a piece of tissue, a sample of cells, and/or fluid from the body so that it can be further analyzed. Biopsies are typically used to assist in the identification and diagnosis of a disease state, and while medical imaging technologies are helpful in detecting masses or areas of abnormality, they alone cannot differentiate, for example, cancerous cells from noncancerous cells. For the majority of cancers or other dysfunctions, a more certain way to make a definitive diagnosis is to perform a biopsy to collect cells for closer examination.

There are a number of different invasive and non-invasive biopsy techniques, and based on the tissue region, the depth of the biopsy, and/or the size of biopsy needed, one or more biopsy techniques can be performed. Surgical biopsy is a form of invasive biopsy where a medical professional—typically a surgeon—makes an incision in the skin to access a suspicious area of cells. Surgical biopsy procedures can be used to remove part of an abnormal area of cells (i.e., incisional biopsy), or surgical biopsy may be used to remove an entire area of abnormal cells (i.e., excisional biopsy). Examples of surgical biopsy procedures include surgery to remove a breast lump for diagnosing breast cancer and surgery to remove a lymph node for diagnosing lymphoma. For obvious reasons, such as an increased risk of infection, additional wound healing, and the inability to access some sites without serious disruption to surrounding tissue, surgical biopsy is often a less desirous option for obtaining questionable tissue for pathological assessment.

Other less invasive forms of biopsy are available and routinely used in the clinical setting. Endoscopic biopsy is an exemplary form of non-invasive or less invasive biopsy that utilizes a thin, flexible tube (i.e., an endoscope) with a light on the end to visualize structures inside the body and which are typically not easily accessible at or near the skin. Specialized cutting tools can be passed through the tube for biopsy extraction. Depending on the location of interest, endoscopic biopsy can be performed by inserting the endoscope through the mouth, rectum, urinary tract, or a small incision in the skin.

Other forms of non-invasive biopsy include needle biopsy. During a needle biopsy, a specialized needle is used to extract cells from a suspicious area. In some cases, needle biopsy is combined with an imaging procedure such as ultrasound or various x-ray based imaging technologies, magnetic resonance imaging, or computed tomography to help guide biopsy selection in areas that are difficult to feel through the skin or are otherwise difficult to accurately and precisely sample (e.g., due to size, shape, location, etc.). Image-guided biopsy techniques are often utilized, for example, when taking a biopsy of abnormalities in the liver, lung, prostate, and breast.

An exemplary type of needle biopsy includes core needle biopsy, which utilizes a larger needle (e.g., less than 20 G, as known in the art) with a specialized cutting tip that houses a trough where a column of tissue can be extracted from an area of interest. However, core needle biopsy and the currently available tools for implementing this technique are generally not safe for vital or delicate soft tissues in the body, as they can cause significant trauma to the tissue during biopsy extraction. In some instances, the size and method of action of core needle biopsy tools, themselves (e.g., the large gauge of the needle and the relatively large biopsy obtained thereby), are individually and/or collectively too disruptive or difficult to implement at the sample site.

Other types of needle biopsy include fine needle aspiration (FNA). During FNA, a long, thin needle is inserted into the suspicious area, typically through the skin. A syringe is used to draw out fluid and cells for analysis. A similar type of biopsy includes fine needle nonaspiration (FNNA), which utilizes the needle alone—without the use of a syringe—to extract cells, tissue, and/or fluid from the biopsy site. FNNA relies, in some instances, on capillary action to draw cells, tissue, and/or fluid into the hollow region of the needle. In both FNA and FNNA, the needle is inserted at or near the desired biopsy site and reiteratively probed up and down, forcing the biopsy material into the hollow of the needle. This method, while less traumatic on vital or delicate soft tissue than a core needle biopsy, is inefficient, time consuming, and resource intensive.

Additionally, there is a striking lack of tools particularly crafted for use in fine needle biopsy. As a result, medical professionals are left with no other option than to grasp a standard fine needle between opposing digits to perform fine needle biopsy. Thus, employing fine-needle biopsy in a clinical setting requires precise digital manipulation with a deft hand and can take years of experience to acquire proficiency. Improper technique can lead to collateral tissue damage or infection, and even when properly implemented, fine needle biopsy can cause unexpected trauma at the biopsy site. A biopsy device designed specifically for fine needle biopsy is needed that can offer structural support, stability, and versatility in its implementation and which can improve the efficiency of performing fine needle biopsies.

Accordingly, there are a number of disadvantages in the art of biopsy devices that can be addressed.

BRIEF SUMMARY

Embodiments of the present disclosure solve one or more of the foregoing or other problems in the art with systems and apparatuses for performing biopsies, including retrievable single stick fine needle biopsy. An exemplary biopsy device disclosed herein can include (i) an elongated body, (ii) a hollow needle coupled to the distal end of the elongated body, the hollow needle having a channel that spans the length of the hollow needle, (iii) a trigger associated with the elongated body, (iv) a stylet having or associated with a biopsy element, the stylet being disposed within the channel of the hollow needle, operably connected to the trigger, and configured to extend beyond the distal end of the hollow needle and subsequently retract within the channel of the hollow needle, and (v) a spring mechanism operably connected to the trigger such that the spring mechanism compresses in response to operation of the trigger, extending the biopsy element, and is configured to rebound following compression, the rebound causing the biopsy element to retract toward or within the hollow needle.

For example, such a biopsy device and other biopsy devices and systems disclosed herein provide enhanced digital manipulation of fine needles used to biopsy. The biopsy device is sized and shaped to be comfortably held and operated in a manner that is natural to the operating physician and can be adapted for multiple different handheld positions and In some instances, biopsy devices provided by the present disclosure include a first trigger or plunger associated with the proximal end of the elongated body and a second trigger associated with the distal end of the elongated body that moves co-dependently with the first trigger.

Additionally, or alternatively, biopsy devices can include a core body coupled to the stylet and disposed within the lumen between the first trigger and the second trigger, the core body comprising a stopper configured to interact with and compress the spring mechanism when either the first trigger or the second trigger is activated.

Biopsy devices can also include an attachment base coupled to the hollow needle and operably connected to the spring mechanism.

In some instances, a biopsy device is associated with a removable sheath or retractable cover. The retractable cover can be configured to occlude a distal tip of the hollow needle in a first position and to expose at least the distal tip of the hollow needle in a second position. The retractable cover can, in some embodiments, define an aperture having a larger diameter than the diameter of the hollow needle and can be positioned to slidably transition between a first position to a second position (e.g., along the attachment base) such that the distal tip of the hollow needle traverses the aperture when transitioning between the first position and the second position.

The stylet of biopsy devices disclosed herein can include a biopsy element. This can include, for example, a spiral tip biopsy element, an alligator biopsy element, a second hollow needle, or a core biopsy needle. It can also include an expanded spiral tip having a low friction surface configured to reduce an amount of energy necessary to transit a biopsy from a distal portion of the expanded spiral tip to or along a proximal portion of the expanded spiral tip.

The hollow needle can be or include a metallic, hollow needle, and/or the biopsy element can be or include a smaller metallic, hollow fine needle.

The trigger can include a locking mechanism that can be configured to engage, thereby retaining the spring mechanism in a compressed configuration, upon a first pressure threshold being exceeded.

Some embodiments include biopsy systems. An exemplary biopsy system can include a biopsy device and a sheath configured to associate with the biopsy device and to cover at least a portion of the biopsy device needle. The biopsy device of the biopsy system can include (i) an elongated body with a distal end and a proximal end; (ii) a drive mechanism that includes a core body disposed within a lumen defined by the elongated body, an attachment base associated with the distal end of the elongated body, and a spring mechanism disposed between and operably connected to the attachment base and the core body; (iii) a hollow needle coupled to the attachment base and defining a channel that extends the length thereof; (iv) a stylet coupled to the core body and disposed at least partially within the channel and which has or is coupled to a biopsy element at a distal tip thereof; (v) a first trigger associated with the proximal end of the elongated body and operably connected to the core body; and (vi) a second trigger associated with the attachment base and operably connected to the core body. In some embodiments, the second trigger is configured to move co-dependently with the first trigger and/or the spring mechanism is configured to compress in response to operation of the first trigger or the second trigger—the compression causing the biopsy element to extend away from a distal end of the hollow needle—and to rebound following compression—the rebound causing the biopsy element to retract toward or within the distal end of the hollow needle.

Methods for obtaining a biopsy sample are additionally provided and include at least the step of using any one of the biopsy devices and/or biopsy systems disclosed herein.

Accordingly, biopsy devices and systems—and methods for using the same—are disclosed. Additional features and advantages of the disclosure will be set forth in the description that follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. These drawings depict only typical embodiments of the disclosure and are not therefore to be considered limiting of its scope. The disclosure will be described and explained with additional specificity and detail through the use of the accompanying drawings in which:

FIG. 1 illustrates an exemplary biopsy device with a magnified view of the tip thereof depicted in balloon A;

FIG. 2 illustrates the exemplary biopsy device of FIG. 1 with the trigger activated and with a magnified view of the tip thereof depicted in balloon B;

FIG. 15 illustrates an exploded view of another exemplary biopsy device;

FIG. 16 illustrates a cross-sectional perspective view of the assembled biopsy device of FIG. 15;

FIG. 17 illustrates a magnified cross-sectional perspective view of the distal end of the assembled biopsy device of FIG. 15;

FIG. 18 illustrates an exploded view of yet another exemplary biopsy device;

FIG. 19 illustrates a cross-sectional perspective view of the assembled biopsy device of FIG. 18;

FIG. 20 illustrates a magnified cross-sectional perspective view of the distal end of the assembled biopsy device of FIG. 18;

DETAILED DESCRIPTION

Figure 3:
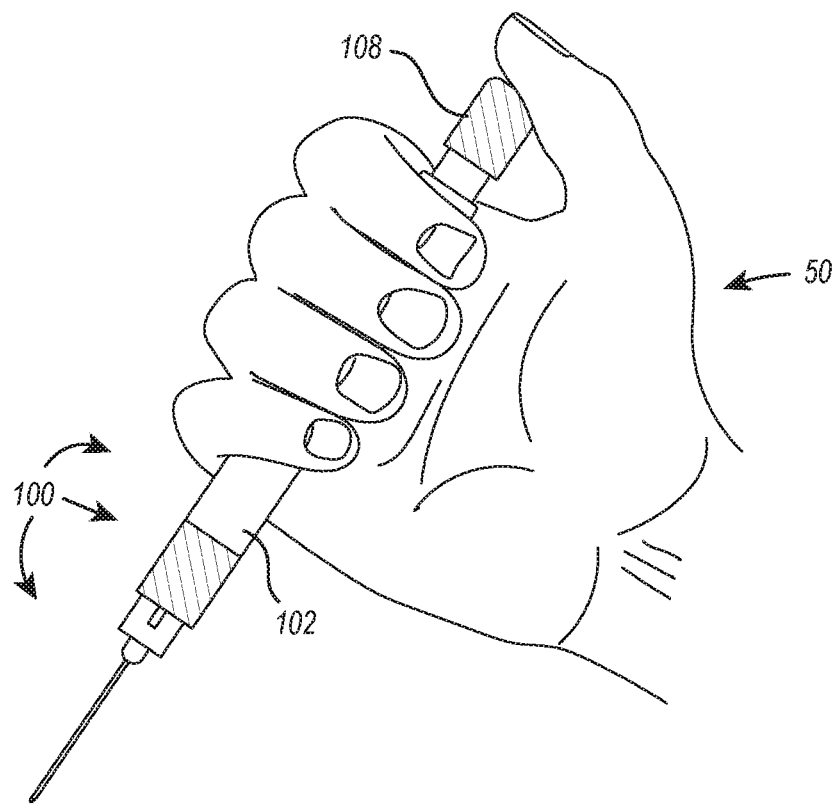
FIG. 3 illustrates an exemplary use of biopsy devices disclosed herein.

As briefly described above, fine needle biopsy is a sub-category of non-invasive needle biopsy techniques that utilize thin hollow needles to collect a biopsy from a target tissue site. Fine needle aspiration (FNA), one type of fine needle biopsy, utilizes a long, thin needle to access and biopsy suspicious areas, typically through the skin. A syringe is used to apply negative pressure and draw out fluid, cells, and tissue for analysis. A similar type of fine needle biopsy includes FNNA, which utilizes the long, thin needle alone—without the use of a syringe—to extract cells, tissue, and/or fluid from the biopsy site. In some instances, FNNA relies on capillary action, instead of the negative pressure utilized in FNA, to draw cells, tissue, and/or fluid into the hollow region of the needle. Regardless, both FNA and FNNA force biopsy material into the hollow of the fine needle via reiterative up and down probing at the biopsy site. This method causes tearing and disruption of surrounding tissue as the beveled needle repeatedly jabs the target site to secure sufficient biopsy material.

Implementing this technique in the clinical setting requires a high level of coordinated dexterity and often years of experience to efficiently—or even properly—perform. Furthermore, even when properly executed, and regardless of whether the physician opts for using negative pressure via an attached syringe (e.g., as in FNA) or simply utilizing the needle, itself, (e.g., as in FNNA), it is often difficult to obtain sufficient biopsy material for an accurate diagnosis using a single needle. This forces multiple successive attempts (often three or more), and due to procedural guidelines governing aseptic technique, a new, sterile needle is likely used for each successive attempt. This increases the time for the procedure, the cost associated with the procedure (from both a labor and materials perspective), and undoubtedly increases the impact of the procedure on the patient (e.g., increased discomfort, pain, and potentially a higher risk of related trauma or infection).

Further, there is a lack of surgical tools tailored for use in fine needle biopsy procedures. In fact, the tools used in both FNA and FNNA include hollow needles and syringes (for FNA) that are standard in most clinical settings. There is no known single stick fine needle biopsy device available for use with superficial soft tissues, and current methods and devices are time consuming, resource intensive, and unsafe for delicate structures of the body, especially close to large blood vessels which are common in the neck and chest and vital organs such as the heart.

An estimated 600,000 fine needle biopsy procedures are performed annually on the thyroid, alone, and each of these fine needle biopsies suffer from the same foregoing methodological and device pitfalls discussed above. There is a long felt, unmet need in the field of fine needle biopsy for devices and kits that alleviates one or more of the aforementioned disadvantages or that, at the very least, increases procedural efficiency, reduces procedural cost, and/or lessens the impact of the procedure on the patient.

Embodiments of the present disclosure provide biopsy devices that can efficiently extract biopsy material from a target site in a retrievable single stick while doing so in a manner that is safe for vital or delicate tissues. Embodiments of the present disclosure can further minimize trauma at the biopsy site compared to prior art methods and devices, reduce potential complications associated with fine needle biopsy, and increase the efficiency of fine needle biopsy procedures (e.g., reduced time per procedure, lower skill threshold for proper and/or efficient use, increase operator control, increase versatility, reduced labor, and reduce materials required to perform biopsies).

In general, embodiments of the present disclosure are operable to selectively extend and retract a biopsy element through the hollow of a fine needle. The biopsy element is, thereby, configured to extend beyond a beveled edge of the hollow, fine needle and retrieve a biopsy of a target site when in an extended position and is additionally configured to retract back within the hollow of the fine needle for extraction from the body. The biopsy element can be reiteratively extended and retracted into the biopsy site to retrieve additional biopsy sample while the hollow needle remains stationary. In this manner, the biopsy devices disclosed herein can obtain sufficient biopsy sample with a single stick (e.g., the hollow needle inserted at the biopsy site) in a manner that, among other things, reduces trauma and risk of infection.

In some embodiments, the biopsy devices disclosed herein are operable to reiteratively retrieve a biopsy at the same or a different site without changing needles such that a plurality of biopsies can be quickly retrieved with each individual biopsy being retrieved in a single stick. Disclosed biopsy devices can also include interchangeable stylets and/or interchangeable biopsy elements. Additionally, or alternatively, disclosed biopsy devices can be disposable after a single use and can be specially designed and marked for various sizes and/or types of needles and biopsy elements.

Biopsy devices disclosed herein can also beneficially include a rotation mechanism that causes the biopsy element (and one or more other elements associated therewith) to rotate in addition to traversing laterally. In doing so, the rotation mechanism can increase the cutting/acquisition efficiency of the biopsy element when retrieving a biopsy. The biopsy element can be a hollow needle or a spiral tip that corkscrews through tissue when rotating to thereby retrieve a biopsy sample. The biopsy element may also be an alligator biopsy element having a plurality of separable mandibles that are biased away from one another when the alligator biopsy element extends beyond the channel of the hollow needle, and upon being drawn back into the channel, the mandibles regain a tighter association. The biopsy element may also be a distal core biopsy needle. The rotational movement of the biopsy element, in addition to the various types of biopsy elements that can be used, advantageously allows for improved retrieval of biopsy samples from delicate structures and can additionally reduce trauma at the biopsy sample site.

Further, some biopsy devices disclosed herein provide a dual trigger, one being a plunger disposed at the proximal end of the device body and one being a sliding trigger disposed at a proximal end of the device body. The triggers can move independently or co-dependently and can be operable to project the biopsy element from the tip of the hollow needle, and the placement of the triggers affords the physician improved versatility and stability when using the biopsy device. Such biopsy devices can be held and operated in different configurations, depending on access to the biopsy site and/or comfort of the physician. This can advantageously enable more physicians to properly perform FNNA biopsies with a reduced level of coordinated dexterity and experience, which has to date prevented many physicians from performing FNNA biopsies.

Various additional features and embodiments of biopsy devices described herein are provided below and may make reference to the accompanying figures, when necessary.

Exemplary Fine Needle Biopsy Devices

Embodiments of the present disclosure enable biopsy devices and biopsy systems. For example, FIGS. 1 and 2 illustrate an exemplary biopsy device 100.

Referring now to FIG. 1, illustrated is biopsy device 100, which includes an elongated body 102 having a proximal end 104 and a distal end 106. A first trigger 108 is associated with the proximal end 104 of the elongated body 102, and a second trigger 110 is associated with the distal end 106 of the elongated body 102. The biopsy device 100 additionally includes hollow needle 112 associated with the distal end 106 of the biopsy device 100. As more clearly illustrated in the magnified view A of FIG. 1, the hollow needle 112 defines a channel into which a stylet 114 is at least partially disposed.

The triggers 108, 110 are operably connected to the stylet 114 such that when the triggers are activated, a tip or biopsy element 115 of the stylet 114 is exposed and/or extends away from the distal end of the hollow needle 112, as shown between FIGS. 1 and 2 and as illustrated in the respective magnified views A, B. The first trigger 108 can move co-dependently with the second trigger 110, as shown in FIG. 2, such that activation of either trigger 108, 110 causes movement of the stylet 114. The triggers 108, 110 can also be configured to move independently from each other such that activation of either trigger causes the stylet 114 to move but does not cause a similar movement of the non-activated trigger.

Although biopsy devices disclosed herein can be configured to include a single trigger (not shown), a preferable dual trigger embodiment (e.g., biopsy device 100 of FIGS. 1 and 2) beneficially provides versatility in implementation. For example, as shown in FIG. 3, a physician 50 can grasp the biopsy device 100 like a pen with the fingers and palm of the physician's hand wrapped around the elongated body 102 and the thumb positioned over the first trigger 108. The physician 50 can then move the biopsy device 100 into position at the biopsy site and retrieve a biopsy sample by depressing the first trigger 108, similar to activating a plunger of a mechanical pen.

Figure 4:
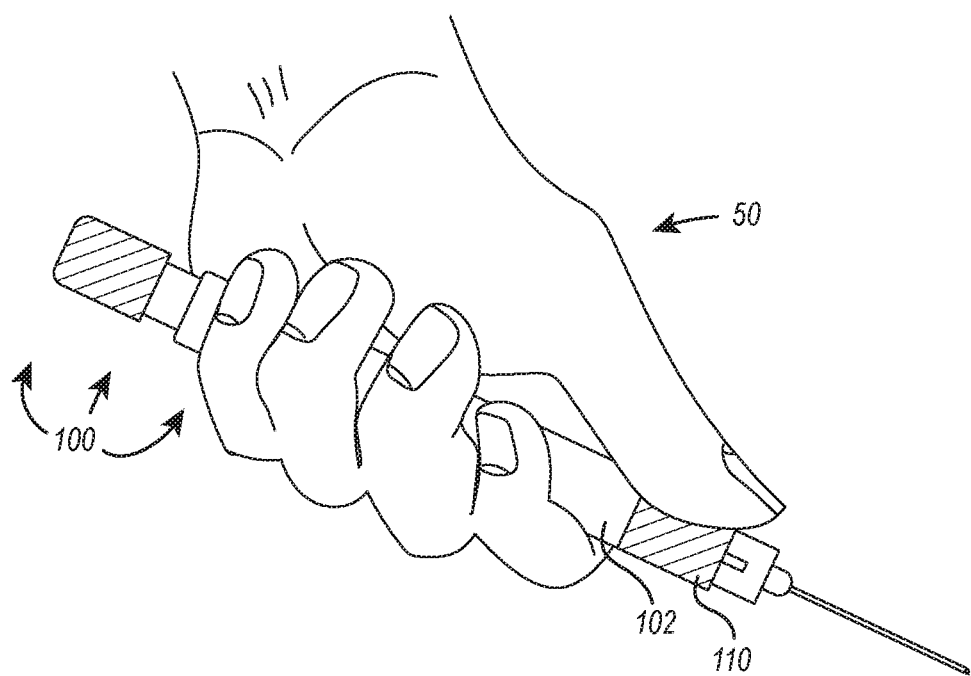
FIG. 4 illustrates another exemplary use of biopsy devices disclosed herein.

Alternatively, as shown in FIG. 4, the physician 50 can grasp the biopsy device 100 with the fingers and palm of the physician's hand wrapped around the elongated body 102 and the thumb pointed toward and resting on the second trigger 110. The physician 50 can then deftly handle the biopsy device 100 into position at the biopsy site and retrieve a biopsy sample by, for example, sliding her thumb toward the distal tip of the hollow needle 112.

FIGS. 3 and 4 illustrate two exemplary uses of the disclosed biopsy devices, but it should be appreciated that there are other uses and manners of operating disclosed biopsy devices than those shown in FIGS. 3 and 4. Nevertheless, FIGS. 3 and 4 illustrate some advantages offered by the disclosed biopsy devices. For example, the biopsy device can be manipulated into position at the biopsy site in a manner that is more comfortable to the individual physician and which offers the individual physician with a greater sense of control and stability. Moreover, the physician can control the speed and, to some degree, the depth at which the biopsy element is extended into tissue by directly controlling the rapidity and distance the first trigger 108 is depressed and/or the second trigger 110 is moved.

Additionally, by repeatedly activating the trigger, the physician can cause reiterative extension of the biopsy element to obtain a plurality of biopsy samples and can do so with greater control. This is, at least in part, due to the ability of the physician to grasp the biopsy device with a large portion of her hand as opposed to manipulating a small needle between a few digits as done in prior art methods. Furthermore, the biopsy device can be similar in size and/or shape to a pen, which the physician will likely have prior experience and familiarity handling. This familiarity can beneficially operate to increase the physician's aptitude for comfortably and/or confidently handling the biopsy device, which, for example, translates into higher efficiency biopsies performed with greater proficiency.

Figure 5:
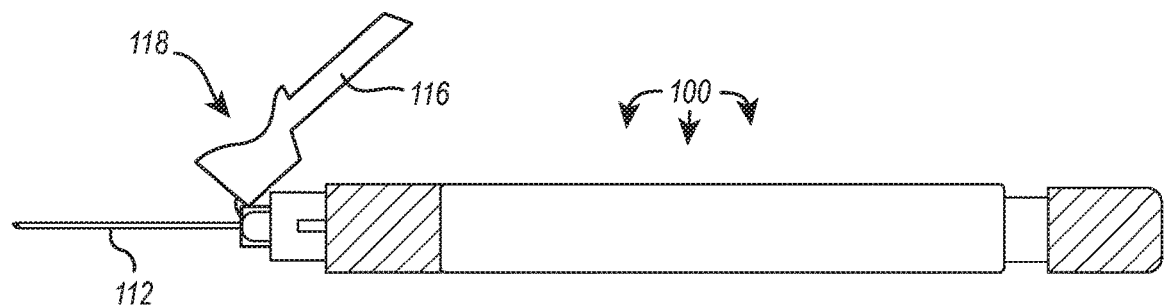
FIG. 5 illustrates an open, hinged safety cover associated with an exemplary biopsy device.
Figure 6:
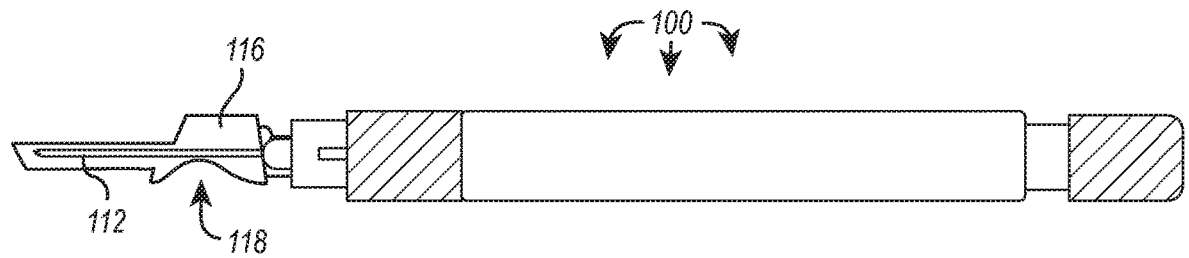
FIG. 6 illustrates the exemplary biopsy device of FIG. 5 with the hinged safety cover depicted as closed and/or covering the distal end thereof.

Biopsy systems disclosed herein can include a biopsy device configured to fit or associate with a sheath or cover, for example, to prevent inadvertent needle sticks and/or to reduce contamination of the needle or biopsy element before and/or after use. FIGS. 5 and 6 depict an exemplary biopsy device 100 that includes a rotatable needle cover 116 associated with the hollow needle 112. The hollow needle 112 can be exposed for use (as shown in FIG. 5) by hinging the rotatable needle cover 116 away from the hollow needle 112. The rotatable needle cover 116 can include a groove 118 to facilitate movement of the cover 116, which as depicted in FIGS. 5 and 6 can be sized and shaped to accommodate a user's thumb or other digit. When not in use, the cover 116 can be rotated back into place over the hollow needle 112, as shown in FIG. 6.

The rotatable needle cover 116 can include a locking mechanism to retain the cover 116 in a closed configuration over the needle 112. The locking mechanism can include, for example, the base of the cover 116 forming an interference fit with a distal portion of the biopsy device and/or with the hollow needle 116, itself. Other locking mechanisms are known in the art and can be adapted for use with the biopsy devices disclosed herein.

Figure 7:
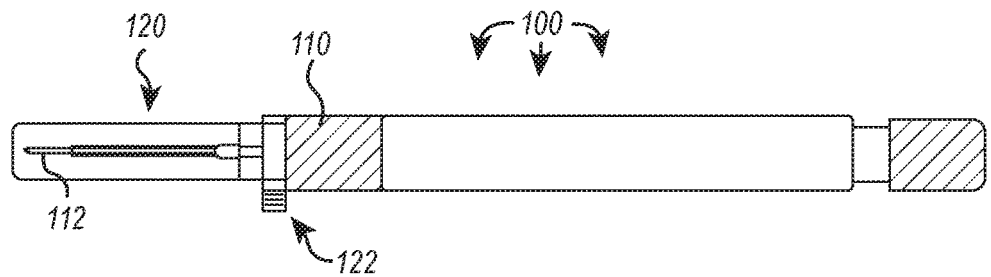
FIG. 7 illustrates an exemplary biopsy device having a safety-sealed sheath associated with the distal end thereof.
Figure 8:
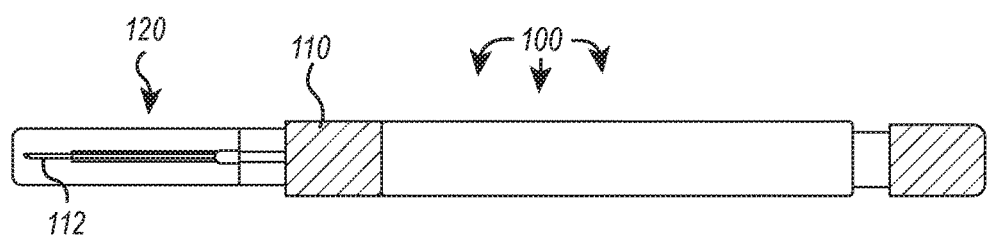
FIG. 8 illustrates the exemplary biopsy device of FIG. 7 having a sheath associated with the distal end thereof, the safety-seal having been removed.

Referring now to FIGS. 7 and 8, illustrated is an additional example of a biopsy system having a biopsy device 100 associated with a cover 120 to protect the needle 112 (and others) when not in use. Before use, the biopsy device 100 can be securely fitted with a cover 120 that is positioned to abut the second trigger 110 (or in some embodiments the distal end of the elongate body) and additionally locked or otherwise secured in place by a removable safety tag 122. In some embodiments, removal of the cover 120 causes the tag 122 to break and/or to remove the cover 120, the tag 122 must first be broken or removed. In any event, the removable safety tag 122 can serve as a visual confirmation of whether the associated biopsy device 100 has been used or whether it has potentially been contaminated. If the removable safety tag 122 is absent or broken (as shown in FIG. 8), the associated biopsy device 100 can be processed and/or disposed of.

Upon removal of the cover 120, the biopsy device 100 can be used, as described herein. After use, the cover 120 can be replaced (as shown, for example, in FIG. 8). This protects the obtained biopsy sample from contamination and can additionally act to prevent inadvertent sticks with the needle 112 during transport and/or processing. Additionally, when the cover 120 is associated with the biopsy device, it can act as a physical barrier to prevent movement of the second trigger 110—in essence locking the biopsy device. This can prevent the stylet and/or biopsy element (not shown) from inadvertently extending and breaking, disfiguring, or ejecting biopsy sample.

Additionally, or alternatively, biopsy devices can include a locking mechanism associated with one or multiple triggers. For example, an exemplary locking mechanism can be associated with the first (and/or second) trigger and include at least a first pressure threshold. The trigger can be activated by exerting a first pressure on the trigger, and upon reaching the first pressure threshold a distance away from the resting, unactivated position of the trigger, the trigger will be prevented from further activation given the same first force. Exerting additional force, the combination of which exceeds the first pressure threshold, causes the locking mechanism to engage and retain the trigger in a locked position. The locking mechanism can be disengaged, for example, by exerting a second force against the trigger or by pressing a release button. The second force can be, in some instances, in an opposite direction of the first force, or the second force can be in the same direction as the first force and beyond a second pressure threshold, the second pressure threshold being greater than the first pressure threshold.

A locking mechanism such as the aforementioned locking mechanism can allow a biopsy device to be positioned and maintained in a configuration where the stylet and/or biopsy element is extended beyond the distal tip of the hollow needle. This locked configuration can be beneficial, for example, for extracting the collected biopsy samples or for inspecting the biopsy element.

Other needle covers and associated biopsy devices are envisioned by the present disclosure. For example, as shown in FIGS. 9-20, a biopsy device 200, 300, 400 can be associated with a retractable cover 220, 320, 420. In an exemplary embodiment shown in FIGS. 9-14, a biopsy device 200 can include an elongate body 202 having a proximal end 204 and a distal end 206, a first trigger 208, and a second trigger 210—any of which can be the same or similar to the elongate body 102 having a proximal end 102 and a distal end 106, the first trigger 108, and the second trigger 110, described above. The biopsy device 200 can further be associated with a retractable cover 220.

Figure 9:
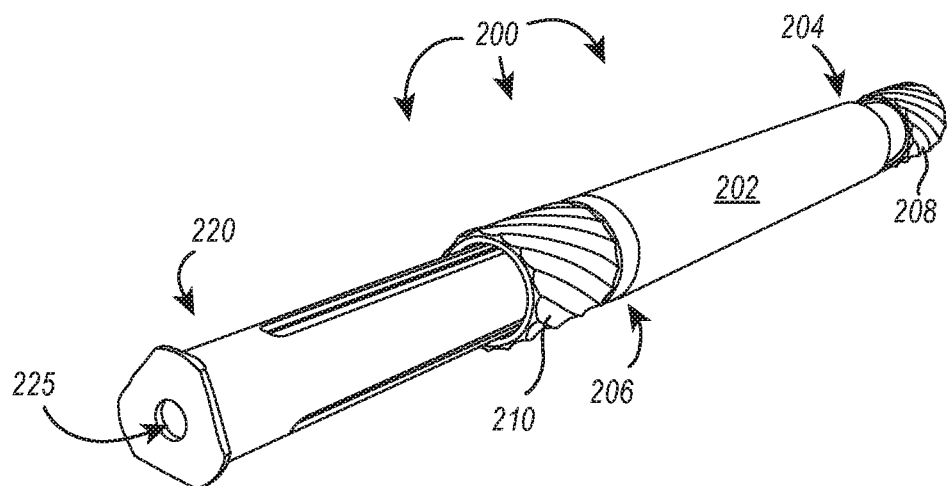
FIG. 9 illustrates another exemplary biopsy device with a retractable cover.
Figure 10:
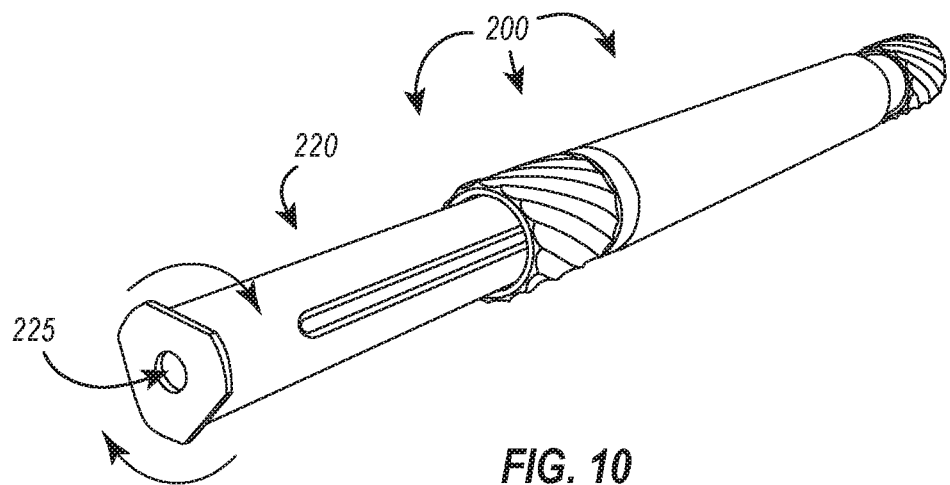
FIG. 10 illustrates the exemplary biopsy device of FIG. 9 with the retractable cover being rotated as a first step in exposing the needle covered thereby.
Figure 11:
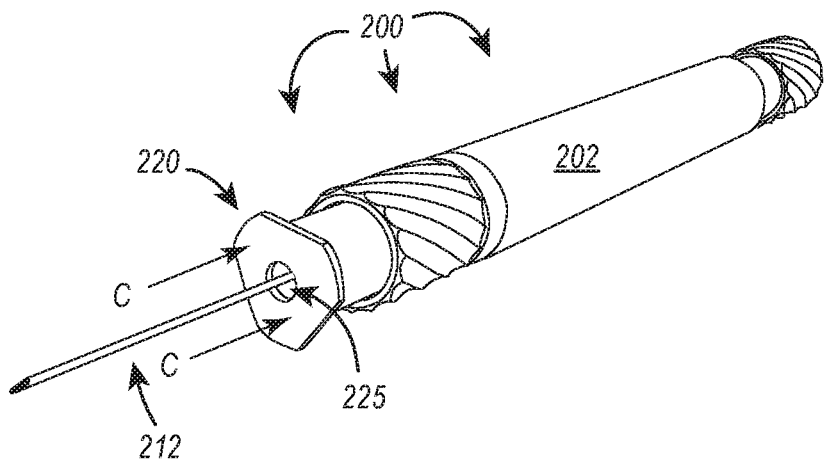
FIG. 11 illustrates the exemplary biopsy device of FIG. 10 with the retractable cover being retracted and locked.

As shown in FIGS. 9-11, the retractable cover 220 can be in a resting or unused configuration, shown in FIG. 9, where the retractable cover 220 cannot move, or is prevented from moving, laterally (i.e., retracting) with respect to the hollow needle 212. Rotating the retractable cover to from the resting or unused configuration to a first position, as shown in FIG. 10, positions the retractable cover 220 so that it can be retracted within the body of the biopsy device 200, as shown in FIG. 11. The mount or degree of rotation for moving from a resting or unused configuration to the first position can vary by embodiment and can include a clockwise or counterclockwise rotation. As shown in FIG. 10, the retractable cover 220 is rotated 45° clockwise from the configuration of FIG. 9 to reach the first position. It should be appreciated that the first position can be configured at any amount or degree of rotation in either a clockwise or counterclockwise direction ranging from 1° to 359°, preferably between 30° and 270°, more preferably between 45° and 180°.

As further illustrated by FIGS. 10 and 11, the retractable cover 220 defines an aperture 225 having a larger diameter than the diameter of the hollow needle 212. When the retractable cover 220 is positioned to slidably transition between the first position (as shown in FIG. 10) to the second, retracted position (as shown in FIG. 11), a force exerted against the retractable cover 220 (illustrated by arrows C in FIG. 11) permits the distal tip of the hollow needle 212 to traverse the aperture 225, thereby revealing the hollow needle 212. In some embodiments, the retractable cover 220 can freely slide between the first and second positions. It may be desirable, however, to lock the retractable cover 220 in a retracted configuration, such as when performing a biopsy. The retractable cover 220 can, therefore, be configured to lock in a retracted configuration in some embodiments. This can be achieved by any means known in the art, including, for example, by being received in an interference fit with a component disposed within the body of the biopsy device or by further rotating the retractable cover in the second configuration to engage a mechanical locking mechanism. In the latter embodiment, the retractable cover may be unlocked/released from the locking mechanism, for example, by rotating the retractable device back to the second configuration.

Figure 12:
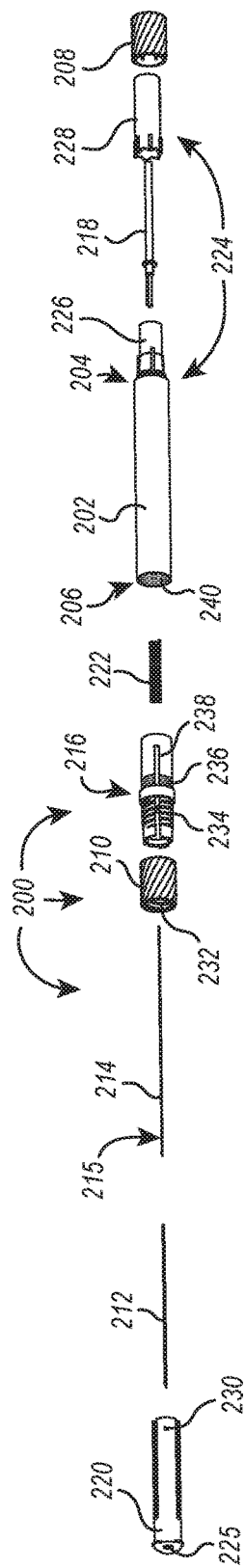
FIG. 12 illustrates an exploded view of an exemplary biopsy device.
Figure 13:
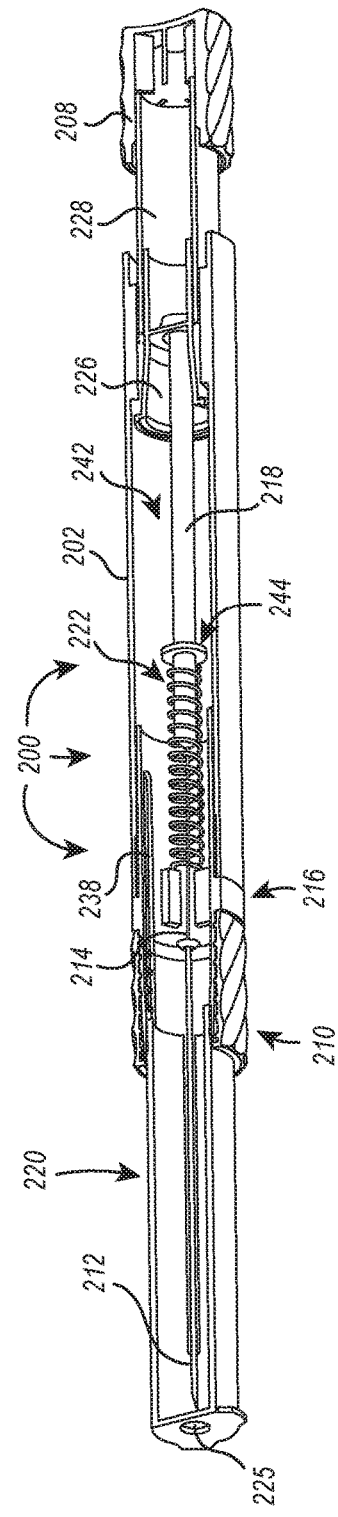
FIG. 13 illustrates a cross-sectional perspective view of the assembled biopsy device of FIG. 12.
Figure 14:
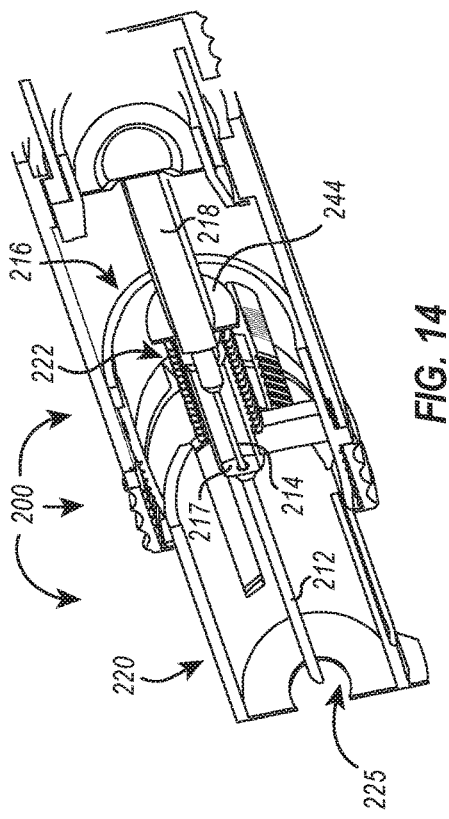
FIG. 14 illustrates a magnified cross-sectional perspective view of the distal end of the assembled biopsy device of FIG. 12.

Referring now to FIGS. 12-14, the biopsy device 200 of FIGS. 9-11 is shown in an exploded view (FIG. 12), an assembled, cross-sectional plan view in the first position (FIG. 10), and an assembled, cross-sectional partial-perspective view (FIG. 11). As illustrated in the assembled views of FIGS. 13 and 14, the biopsy device 200 includes an elongated body 202 threadedly associated with an attachment base 216 at a distal end 206 thereof (e.g., by complementary threads 236, 240) and associated with a trigger mechanism 224 at a proximal end 204 thereof. The first trigger 208 is coupled to a tubular body 228 of the trigger mechanism 224, which is, in turn, slidably associated with an angled-tooth cam 226 of the trigger mechanism 224. The angled-tooth cam 226 is partially disposed within the lumen 242 of the elongated body 202, and a flange of the angled-tooth cam 226 is biased against a sidewall protrusion of the elongated body 202, which prevents it from being dislodged from the proximal end 204 of the elongated body 202. A core body 218 and spring mechanism 222, both of which are disposed within the lumen 242 of the elongated body 202, act in concert to provide the biasing force against the angled-tooth cam 226.

For example, as illustrated in FIG. 13, the spring mechanism 222 is depicted in a rebounded state where the restorative force of the spring mechanism 222 presses against the stopper 244 of the core body 218. In some instances, the restorative force of the spring mechanism 222 is greater than or equal to the opposing weight and/or basal force applied by the combination of the core body 218 and the angled-tooth cam 226 (to which the core body 218 is directly associated) and optionally the tubular body 228 and unactivated first trigger 208. Accordingly, the restorative force can be sufficient to maintain the first trigger 208 in an unactivated position.

With continued reference to FIGS. 12-14, the core body 218 is coupled to a proximal end of a stylet 214. The stylet 214 extends from the coupled proximal end into a channel defined by the hollow needle 212 where it terminates at a distal end including a biopsy element 215. The biopsy element 215 can be disposed within the channel of the hollow needle 212 when the spring mechanism 222 is in its rebounded state (as shown, for example, in FIG. 14). Movement of the core body 218 toward the distal end 206 of the elongated body 202 can cause the stylet to be driven through the channel of the hollow needle 212 to extend beyond the distal tip of the hollow needle 212.

Additionally, illustrated in FIG. 14 is a tapered region 217. The tapered region 217 may assist in directing placement of a stylet 214 within the hollow needle 212. For example, during assembly, a stylet 414 is added to the hollow needle 212. In doing so, the tapered region 217 guides the biopsy element 215 of the stylet 214 through the spring mechanism 222 and into the channel of the hollow needle 212, thereby limiting the degree of micromanipulation necessary to assemble/replace/interchange one or more elements of the biopsy device.

As an illustration of an exemplary use of the biopsy device 200 of FIGS. 12-14, activation of the first trigger 208 (e.g., by applying a mechanical force towards the elongated body 202) transmits force through the trigger mechanism 224 and to the associated core body 218, where the stopper 244 of the core body 218 biases against the proximal end of the spring mechanism 222. The distal end of the spring mechanism 222 is pressed against a stopper or sidewall protrusion of the attachment base 216, preventing lateral movement thereof and causing the spring mechanism 222 to compress. When the activation force of the first trigger 208 exceeds the restorative force of the spring mechanism 222, the core body 218 advances within the lumen 242 of the elongated body. In the process, the stopper 244 of the core body 218 compresses the spring mechanism 222 between itself and the opposing stopper or sidewall protrusion of the attachment base 216.

As described above, the proximal end of the stylet 214 is coupled to the distal end of the core body 218, and the distal end of the stylet 214, including the biopsy element 215, is disposed within the channel defined by the hollow needle 212. At the same time the core body 218 is compressing the spring mechanism 222 and advancing toward the distal end 206 of the elongated body in response to the activation force applied to the first trigger 208, the stylet 214 is forced along in the same direction. This causes the biopsy element 215 to extend beyond the distal tip of the hollow needle 212 where it is then positioned to obtain a biopsy sample.

When the activation force being applied to trigger 208 is relieved, the mechanical energy built up by compression of the spring mechanism 222 (e.g., the restorative force of the spring mechanism 222) is released and applied against the stopper 244, causing the core body 218 to move within the lumen 242 back toward the proximal end 204 of the elongated body 208. At the same time, the stylet 214 is moved in the same direction as the retreating core body 218, causing the biopsy element 215 to retract back into the channel of the hollow needle 212.

The second trigger 210 of the biopsy device 200 is illustrated as being threadedly attached to the attachment base 216 via complementary threads 232, 234. In the illustrated embodiment, the second trigger 210 may not move co-dependently with the first trigger 208. Instead, the second trigger 210 may act as a structural element and/or as a gripping region to assist manipulation of the device when used.

In some embodiments, the second trigger can be modified to associate with a portion of the stylet, core body, spring mechanism, trigger mechanism, and/or first trigger and can be slidably or rotationally associated with the attachment base to cause movement of the stylet within the hollow needle in response to second trigger activation (as described below with respect to at least FIGS. 18-20).

Referring now to FIGS. 15-17, illustrated is a biopsy device 300 that is similar in many respects to the biopsy device 200 described above. For example, the biopsy device 300 includes many of the same or analogous components and is assembled in a similar manner. Accordingly, the disclosure provided for the biopsy device 200 of FIGS. 12-14 can apply in many respects to the components and functionality of the biopsy device 300 of FIGS. 15-17.

Notably, the biopsy device 300 differs from biopsy device 200 by the geometry of the core body 318. As shown in FIGS. 16 and 17, the core body 318 includes three radial projections 344. The radial projections 344 of the core body 318 act in an analogous way to the stopper 244 of core body 218 described above. For example, activation of the first trigger 308 transmits force through the trigger mechanism 324 and to the associated core body 318, where the radial projections 344 of the core body 318 bias against the proximal end of the spring mechanism 322. The distal end of the spring mechanism 322 is pressed against a stopper of the attachment base 316, preventing lateral movement thereof and causing the spring mechanism 322 to compress. When the activation force of the first trigger 308 exceeds the restorative force of the spring mechanism 322, the core body 318 advances within the lumen 342 of the elongated body 302. In the process, the radial projections 344 of the core body 318 compresses the spring mechanism 322 between themselves and the opposing stopper of the attachment base 316. The core body 318 is also coupled to the proximal end of the stylet 314. Thus, the advancement of the core body 318 within the lumen 342 causes a co-dependent advancement of the stylet 314, as described above. Removal of the activation force from the first trigger 308 results in the same reverse movement and retreat of the core body 318 and stylet 314 described above.

Referring now to FIGS. 18-20, illustrated is a biopsy device 400 that is in many ways similar to the biopsy devices 200, 300 of FIGS. 12-17 described above. However, there are some differences. For example, the configuration of the distal end of the retractable cover 420 is shown as being arcuate with an outwardly projecting flange. Alternatively, the biopsy device 400 can be associated with a tubular retractable cover 421. It should be appreciated that the retractable covers 220, 320, 420, 421 include a similar conformation and sliding association with the biopsy devices disclosed in FIGS. 12-20. Accordingly, each of the retractable covers 220, 320, 420, 421 are expected to be interchangeable between the disclosed embodiments.

The biopsy device 400 also includes a conformationally different attachment base 416 than that described above. For example, as shown in FIGS. 19 and 20, the attachment base 416 is threadedly attached to the distal end 406 of the elongated body 402 by complementary threads 436, 440 and to a hollow needle holding member 413 by complementary threads 432, 434. The second trigger 410 is positioned over the body of the attachment base 416 and coupled to the core body 418, which is disposed within the lumen 442 of the elongated body 402. As above, the core body 418 is coupled to a proximal end of the stylet 414, and the proximal end of the stylet 414, including the associated biopsy element 415 are disposed within the channel defined by the hollow needle 412. The proximal end of the core body 418 is associated with a trigger mechanism 424, which, in turn, is connected to the first trigger 408.

The first trigger 408 and the second trigger 410 are operably connected by the core body 418 such that movement of the first trigger 408 causes movement of the second trigger 410, and movement of the second trigger 410 causes movement of the first trigger 408. In other words, the first and second triggers 408, 410 are positioned and configured to move co-dependently with each other.

As an illustration of an exemplary use of the biopsy device 400 of FIGS. 18-20, activation of the first trigger 408 (e.g., by applying a mechanical force on the first trigger 408 towards the elongated body 402) causes the associated core body 418 and associated stopper 444 to bias against the proximal end of the spring mechanism 422. The distal end of the spring mechanism 422 is pressed against the hollow needle holding member 413, which is coupled to the stationary attachment base 416, preventing lateral movement of the spring mechanism 422 and causing it to compress. When the activation force on the first trigger 408 exceeds the restorative force of the spring mechanism 422, the core body 418 advances within the lumen 442 of the elongated body 402. In the process, the stopper 444 of the core body 418 compresses the spring mechanism 422 between itself and the opposing hollow needle holding member 413.

The proximal end of the stylet 414 is coupled to the distal end of the core body 418, and the distal end of the stylet 414, including the biopsy element 415, is disposed within the channel defined by the hollow needle 412. At the same time the core body 418 is compressing the spring mechanism 422 and advancing toward the distal end 406 of the elongated body 402 in response to the activation force applied to the first trigger 408, the stylet 414 is forced along in the same direction. This causes the biopsy element 415 to extend beyond the distal tip of the hollow needle 412 where it is then positioned to obtain a biopsy sample.

Similarly, a force applied to the second trigger 410 is transferred directly to the associated core body 418, causing the core body 418 to compress the spring mechanism 422 and move the stylet 414 through the hollow needle 412, as above.

When the activation force being applied to the first/second trigger 408, 410 is relieved, the mechanical energy built up by compression of the spring mechanism 422 (e.g., the restorative force of the spring mechanism 422) is released and applied against the stopper 444, causing the core body 418 to retreat within the lumen 442 back toward the proximal end 404 of the elongated body 408. At the same time, the stylet 414 retreats in the same direction as the core body 418, causing the biopsy element 415 to retract back into the channel of the hollow needle 412.

Biopsy Devices Containing Rotating Biopsy Elements

Any of the biopsy devices described herein may include or be augmented to include a rotation mechanism, exemplary embodiments of which are depicted in FIGS. 12-20. In general, a rotation mechanism induces rotational movement to the stylet and/or biopsy element when the plunger is depressed and/or relieved and/or when the biopsy element is extended and/or retracted. FIG. 19, for example, illustrates a schematic cross-section of a biopsy device 400 having a rotation mechanism associated with the core body 418 and coupled stylet 414.

The term "rotation mechanism," as used herein includes any mechanical or electromechanical device that provides rotational movement. An exemplary type of rotation mechanism includes click and lock mechanisms. Click and lock mechanisms are provided in many mechanical objects, including, for example, within ball point pens. Generally, click and lock mechanisms work by translating a linear movement into a rotational movement by traversing a series of angled or arcuate surfaces.

An exemplary click and lock mechanism includes a tubular member and angled-tooth cam. During operation, the tubular member is rotationally fixed and only slides up and down, whereas the angled-tooth cam both slides up and down and rotates. Elements fixedly or detachably associated with the angled-tooth cam will also move up and down and rotate. Principally, a downward force is applied to the tubular member, causing it to drive into the cam body. Upon the top of the cam body passing below a stop member threshold, the angled-tooth cam is forced upward, toward the tubular member due to the opposing force applied by a compressed spring mechanism, and because the cam and the tubular member mate at an angle, the cam body slides upward along the angled surface, thereby rotating until the cam body strikes a tubular side wall. This process can be repeated or may have one or more intermediate steps of rotating the cam body until it hits a stop member or other intermediate side wall.

Rotation mechanisms, such as click and lock mechanisms, often have a defined degree of rotation for each translation of linear movement into rotational movement. For example, many click and lock mechanisms rotate 45° for every activation of the trigger (such as the trigger assemblies depicted in FIGS. 14-20). Rotation mechanisms, as used herein, broadly include any degree of rotation per trigger activation, including 60°, 90°, 120°, 150°, 180°, 360°, or any scalar multiple thereof and are not limited to the depicted configurations of FIGS. 14-20. Further, in some embodiments, the rotation mechanism is configurable. For example, a tubular member of the rotation mechanism may include a number of edges and/or stop members that cause the associated cam to rotate 360° for every related linear movement.

An insert can be added or drawn down below and/or flush with the edges of the tubular to increase the number of edges and/or stop members to thereby decrease the degree of rotation for every related linear movement. For example, a first insert doubles the number of edges and/or stop members from one to two, making the associated cam rotate 180° for every related linear movement. Building upon the previous example, a second or alternative insert can be applied similar to the first to, again, double the number of edges and/or stop members from two to four, making the associated cam rotate 90° for every related linear movement. Where the number of edges and/or stop members associated with one or both of the tubular member or the cam are interchangeable and/or configurable, the degree of rotation can be preferentially tailored.

Further, where threads are used to attach one or more of the core body, trigger assembly, trigger, attachment base, or other connected features and where a rotation mechanism is additionally provided, the rotation mechanism may rotate in a single direction that is in the same direction that would act to tighten one or more threaded connections. In this way, retrieving a biopsy does not unintentionally cause the loosening or detachment of any biopsy device components.

Additional Structural and/or Functional Variations of Exemplary Biopsy Elements

Any of the biopsy devices disclosed herein may include one or more biopsy elements with different types of structural and/or functional features, some exemplary embodiments of which are depicted in FIGS. 21-30.

Figure 21:
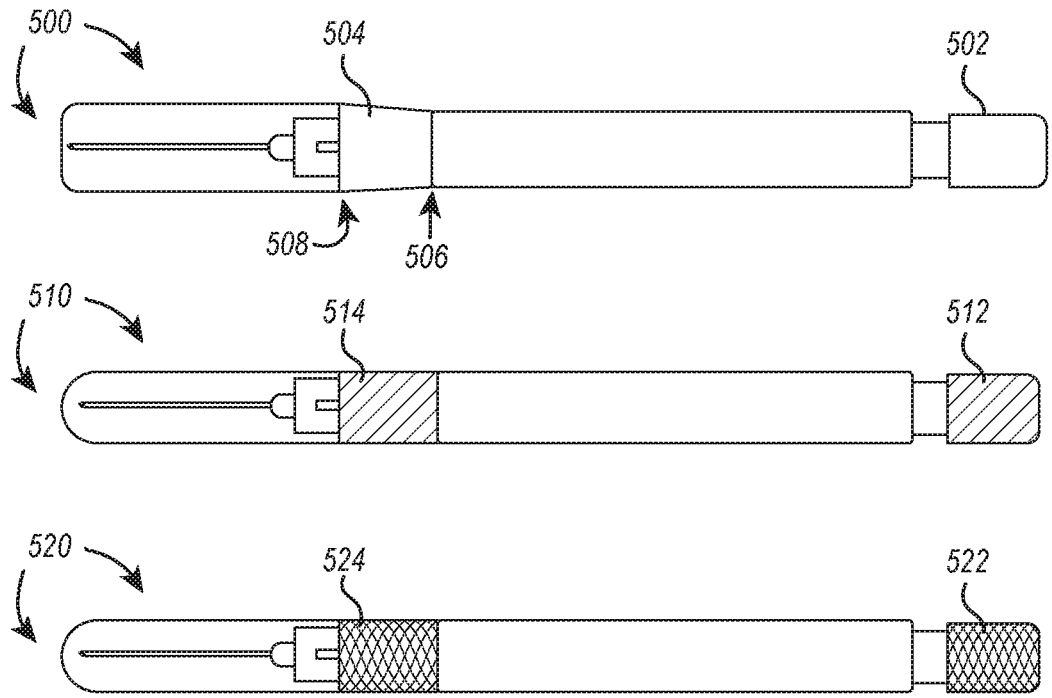
FIG. 21 illustrates a variety of exemplary grips for use with disclosed biopsy devices.

For example, biopsy devices disclosed herein can include one or more contoured surfaces, textures, or grooves associated with various components thereof. FIG. 21 illustrates exemplary biopsy devices having contoured, textured, and/or grooved triggers. As shown, a biopsy device 500 can include a contoured second trigger 504 having a first proximal diameter 506 that is smaller than a second, distal diameter 508. This contoured trigger 504 can beneficially provide an inclined contact surface that makes it easier to activate the second trigger 504 during use. For example, in embodiments where a physician uses her thumb to engage and activate the second trigger, a contoured trigger may more closely follow the contour of her extended thumb than a trigger having a substantially continuous diameter and thereby permit better leverage.

Although the biopsy device 500 illustrates a second trigger 504 as having the contoured shape, it should be appreciated that a distal end of the elongated body may have the same or similar contour (e.g., in embodiments of a single trigger biopsy device). Additionally, or alternatively, the second trigger or elongated body may have other contours than that depicted by the biopsy device 500, such as, for example, a second trigger and/or elongated body having an hour-glass or ergonomic contour.

In addition to, or alternatively from, the contoured components discussed above, biopsy devices of the present disclosure can include components having grooves to increase ease of handling the biopsy device. For example, with continued reference to FIG. 21, biopsy device 510 can include triggers 512, 514 that define a plurality of helical grooves. Alternatively, a biopsy device 520 can include triggers 522, 524 with a knurled pattern on the surface. Each of the foregoing are exemplary modifications that can be made to components of the disclosed biopsy devices that that increase ease of handling the biopsy device, including increased grip.

Other features and modifications can be applied, as known in the art, to increase ease of handling the biopsy device. For example, the elongated body and/or triggers can be shaped to have an angular cross-section (e.g., triangular, quadrilateral, pentagonal, hexagonal, etc.), an arcuate cross-section (e.g., circular, elongate, ellipse-shaped, oblong, etc.), or combinations thereof at the same or different cross-sections that would increase ease of handling. As an additional example, the first trigger can include a concave interaction surface to accommodate a user's thumb when the first trigger is depressed in a fashion similar to a plunger. The second trigger and/or elongated body can additionally, or alternatively, include concave interaction surface(s).

Figure 22:
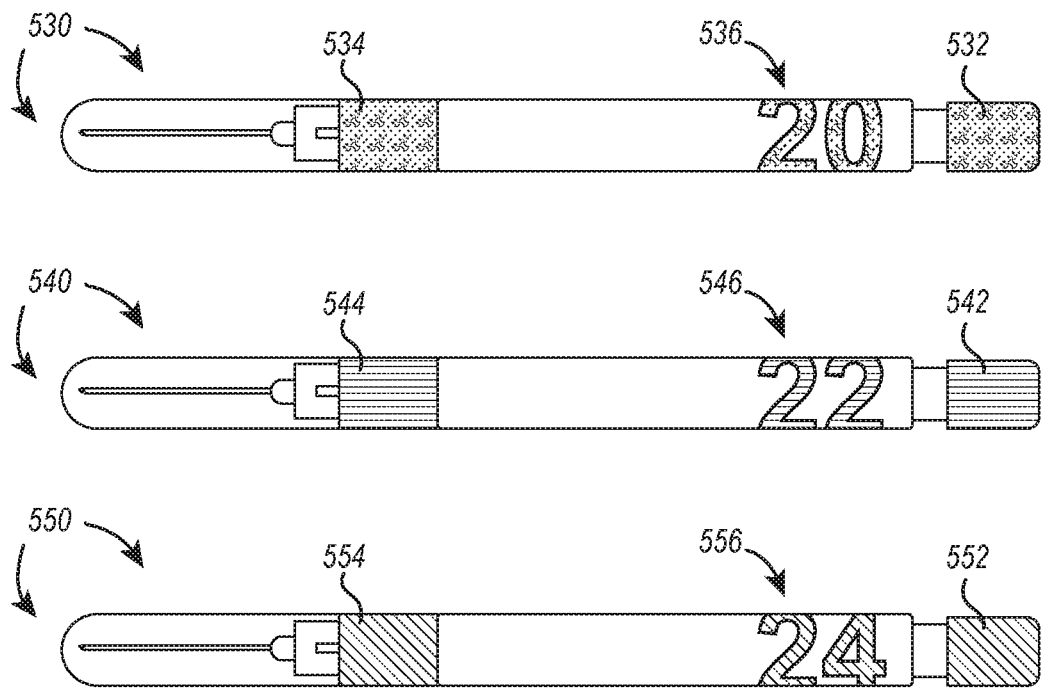
FIG. 22 illustrates an exemplary marking system for differentiating biopsy devices associated with different gauged needles.

In addition to the foregoing, biopsy devices disclosed herein can include aesthetic variations that allow for quick recognition of the type of biopsy device or a distinguishing aspect of the biopsy device. For example, the triggers, elongated body, or other component of the biopsy device can include a pattern or color that indicates the gauge of the hollow needle and/or the gauge of the stylet/biopsy element. As shown in FIG. 22, a biopsy device 530 includes patterned first and second triggers 532, 534 and a similarly patterned number 536 on the elongated body that indicates the gauge of the hollow needle or stylet/biopsy element. Particularly, the biopsy device 530 includes the number "20" on the elongated body, indicating the biopsy device 530 includes a 20 G hollow needle or stylet/biopsy element. Other biopsy devices 540, 550 illustrated in FIG. 22 include different patterns on the triggers 542, 544, 552, 554 and numbers 546, 556 indicative of different gauge hollow needles or stylet/biopsy elements associated with the respective device 540, 550.

In some embodiments, the patterns disclosed above can be replaced by colors. For example, the first and second triggers 532, 534 and the number "20" of biopsy device 530 can be orange, the first and second triggers 542, 544 and the number "22" of biopsy device 540 can be blue, and the first and second triggers 552, 554 and the number "24" of biopsy device 550 can be green. The colors may be different than the foregoing and can be chosen at random. Alternatively, the colors can be chosen based on the International Organization for Standardization (ISO) identified color associated with needle gauges. For example, the biopsy device 530, which includes a 20 G needle can be colored yellow in accordance with the ISO-identified color scheme for a 20 G needle. As additional examples, the colors for biopsy devices 540, 550, which respectively include a 22 G needle and a 24 G needle, can be colored black and medium purple in accordance with the ISO-identified color scheme for 22 G and 24 G needles, respectively.

In some embodiments, the aesthetic variations can indicate a type of biopsy element associated with the biopsy device. This may include an additional aesthetic variation (e.g., mark or color) added to the biopsy device or its associated needle cover.

Aesthetic variations such as those disclosed above can beneficially allow a physician to quickly identify and acquire the proper biopsy device for a given procedure. It can additionally act as a safeguard, allowing the physician and other medical professionals or persons spectating the procedure to identify a distinguishing characteristic of the biopsy device and to prevent an inadvertent use of an improper or unwanted biopsy device. For example, a nurse assisting the physician in a biopsy procedure may be able to quickly compare and verify that the color, pattern, or other distinguishing trait identifying the biopsy device acquired for the procedure is, in fact, the biopsy device requested by the physician or the biopsy device typically used for the given procedure. Accordingly, the aesthetic variations can beneficially allow fast identification of the type of biopsy device and potentially prevent the inadvertent use of the wrong biopsy device.

Figure 23:
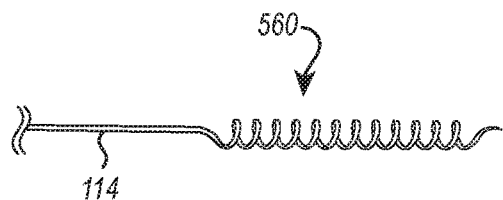
FIG. 23 illustrates a schematic of an exemplary stylet having a spiral tip biopsy element.

Referring now to FIG. 23, illustrated is a schematic of an exemplary stylet 114 having an expanded spiral tip biopsy element 560. Although depicted as being of a given expanded length, the spiral tip biopsy element 560 may be of any suitable length and may include any number of rotations per unit length. In some embodiments, a longer spiral tip may be selected for a larger amount of biopsy material. In some embodiments, a higher number of rotations per unit area can affect the amount of surface area available or "grip" for pulling a biopsy sample from the biopsy site and may increase the efficiency by which a biopsy sample is taken at delicate tissue sites.

During an exemplary implementation of a biopsy device that includes the expanded spiral tip biopsy element 560 of FIG. 23 associated with corresponding stylet 114, the hollow needle of the biopsy device is placed adjacent to a biopsy site. Activation of the trigger causes the stylet to (rotationally) push the spiral tip biopsy element though a distal opening in the hollow needle upon which the spiral tip biopsy element bores into the biopsy site, retrieving cellular material, tissue, and/or fluid in the process. When the trigger is released, the stylet is (laterally—i.e., non-rotationally) retracted, pulling the spiral tip biopsy element back into the channel of the hollow needle together with a retrieved biopsy sample.

Figure 24A:
FIG. 24A illustrates a schematic of an exemplary stylet having a distal alligator biopsy element with the plurality of separably connected mandibles in a closed configuration.
Figure 24B:
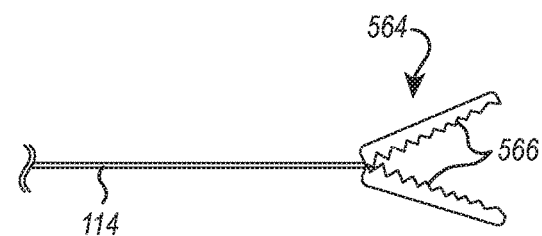
FIG. 24B illustrates is a schematic including the exemplary stylet of FIG. 24A with the plurality of separably connected mandibles biased away from one another in an open configuration.

FIGS. 24A and 24B illustrate schematic views of an exemplary stylet with a distal alligator biopsy element in a closed 562 and open 564 configuration. As shown, the alligator biopsy element includes a plurality of separably connected mandibles with a plurality of teeth 566 defined by each mandible. In some embodiments, the alligator biopsy element includes a plurality of separably connected mandibles biased away from one another in an open configuration. In some embodiments, one of the mandibles is a fixed base with one or more other mandibles biasing away from the fixed base in an open configuration. The number and types of mandibles may vary, and in some embodiments, there may be as many as two, three, or four mandibles.

During an exemplary implementation of a biopsy device that includes the alligator biopsy element of FIGS. 24A and 24B associated with corresponding stylet 114, the hollow needle of the biopsy device is placed adjacent to a biopsy site. Activation of the biopsy device trigger causes the stylet to extend and force the alligator biopsy element through the distal opening of the hollow needle. In some embodiments, the mandibles are spring loaded such that upon exiting the narrow channel, the mandibles separate and open away from each other, thereby defining a biopsy acquisition area. The mandibles are then thrust into and/or placed adjacent to the biopsy site where the mandible teeth can take hold of the soon-to-be-biopsied tissue. Upon releasing the biopsy device trigger, the mandibles close and tear/pull a biopsy sample into the channel of the hollow needle.

In some embodiments, the interaction between the mandibles and the hollow needle (together with the force applied by the spring mechanism expanding) force the mandibles closed. In an exemplary embodiment, an inner diameter of the hollow needle may be enlarged at a portion toward the distal end of the hollow needle, near the sharpened area, to accommodate the biopsied material held between the mandibles when the mandibles are retracted within the distal end of the hollow needle 212. In other words, it may be preferable to provide a vacant volume space within a distal portion of the hollow needle so that when the biopsied material or tissue is drawn into the hollow needle, sufficient space is allowed so that the biopsied material or tissue can be drawn into the hollow needle and thereby be secured and/or protected. In another embodiment, at least a portion of the material disposed at the distal end of the hollow needle can be compressed or elastically stretched, for example in the radial direction, to provide sufficient space to accommodate the biopsied material or tissue held within the mandibles when the mandibles are retracted.

Figure 25:
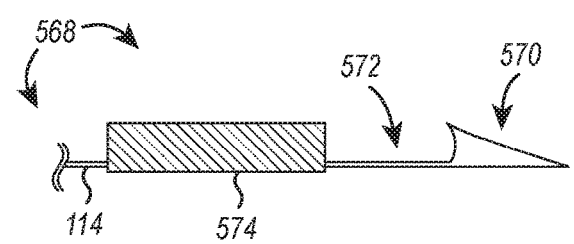
FIG. 25 illustrates an exemplary stylet having a distal core biopsy needle, including biopsy trough and associated outer cutting cannula.

FIG. 25 illustrates an exemplary stylet 114 having a biopsy element 568 that is the same or similar in form and function to a core biopsy needle, including piercing member 570, biopsy trough 572, and associated outer cutting cannula 574. Though depicted as having a single trough 572 for capturing a biopsy core, in some embodiments, the distal core biopsy needle may have any number of troughs (e.g., two, three, four, or five troughs) in the same or different sizes to capture different, or a plurality of, biopsy samples.

During an exemplary implementation of a biopsy device that includes the core biopsy needle 568 of FIG. 25 associated with corresponding stylet 114, the hollow needle of the biopsy device is placed adjacent to a biopsy site. Activation of the trigger causes the stylet to thrust the distal core biopsy needle into the biopsy site where the trough 572 can interact with tissue/cells/fluid to be biopsied. The cutting cannula 574 is then shot down and over the trough 572 (e.g., activated by a trigger on the elongated body/trigger) to acquire the biopsy core sample. Releasing the activated trigger can cause the stylet 114 and the associated core biopsy needle 568 to be drawn back through the channel of the hollow needle.

In some embodiments, the biopsy element can access the same or different biopsy sites multiple times. In doing so, the previously retrieved biopsy can be stored in a biopsy reservoir within the elongated body or located elsewhere on the biopsy device, such as within a vessel coupled to the biopsy element, elongated body, or another portion of the biopsy device. When, for example, the biopsy element is an elongated spiral tip (such as that depicted in FIG. 23), multiple biopsies may be sequentially retrieved with each biopsy being pushed back down the spiral tip as another biopsy is retrieved. In this way, the resulting biopsy core retrieved by the elongated spiral tip consists of multiple biopsy samples taken from a single or a plurality of biopsy sites. To help facilitate the foregoing, at least a portion of the elongated spiral tip may optionally include a low friction surface configured to reduce an amount of energy necessary to transit a biopsy sample from a distal portion of the expanded spiral tip to or along a proximal portion of the expanded spiral tip.

Figure 26:
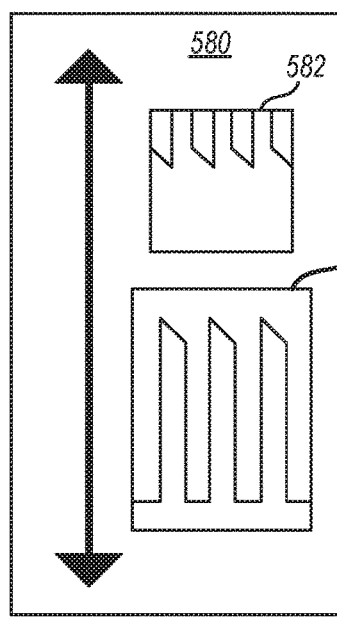
FIG. 26 illustrates a reciprocating drive mechanism for use in disclosed biopsy devices.
Figure 27:
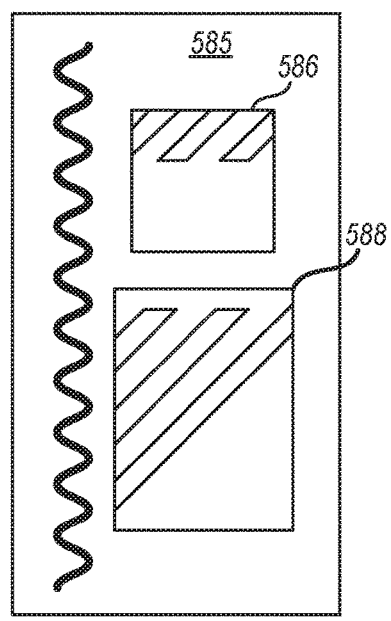
FIG. 27 illustrates a spiral drive mechanism for use in disclosed biopsy devices.
Figure 28:
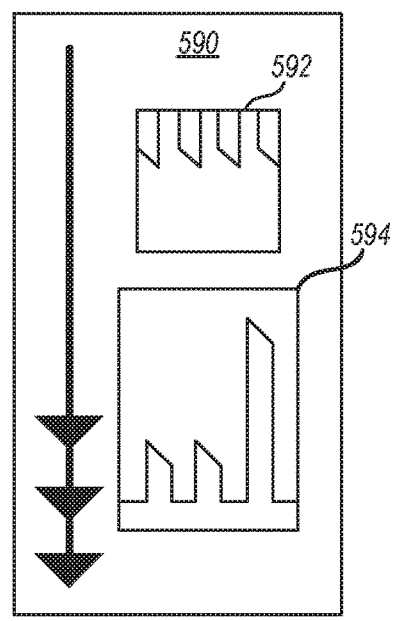
FIG. 28 illustrates a multi-sample drive mechanism for use in disclosed biopsy devices.

Referring now to FIGS. 26-28, a biopsy device can include any one of a plurality of movement profiles 580, 585, 590 following trigger activations. For example, as shown in FIG. 26, a biopsy device may include a set of teeth 582 operably connected to the trigger and/or trigger mechanism that translate directional movement of the trigger to a complementary set of teeth 584 that are operably coupled to the stylet. Due to the configuration of the teeth 582, 584, the forced interaction results in a lateral in-and-out movement depicted by the associated movement profile 580.

As an additional example, FIG. 27 illustrates a spiral movement profile 585 that can be implemented by a biopsy device having a set of angled teeth 586 operably connected to the trigger and/or trigger mechanism that translate directional movement of the trigger to a complementary set of angled teeth 588 that are operably coupled to the stylet. Due to the configuration of the angled teeth 586, 588, the forced interaction results in a spiral movement.

FIG. 27 illustrates an additional example of a spiral movement profile 590 that can be implemented by a biopsy device having a set of differentially sized teeth 592 operably connected to the trigger and/or trigger mechanism that translate directional movement of the trigger to a complementary set of teeth 594 that are operably coupled to the stylet. Due to the configuration of the differentially-sized teeth 592, 594, the forced interaction results in a multi-stage in-and-out movement depicted by the associated movement profile 580. For example, the larger sized tooth illustrated in the movement profile 580 may result in a longer extension of the stylet followed by two shorter extensions of the stylet.

It should be appreciated that biopsy devices disclosed herein can retain the same or similar functionality as those described above but have a different ergonomic and/or aesthetic configuration. For example, a biopsy device 600, illustrated in FIGS. 29 and 30, can include an elongated body 602 having a proximal end 604 and a distal end 606. A first trigger 608 is associated with the proximal end 604 of the elongated body 602, and a second trigger 610 is disposed near the distal end 606 of the elongated body 602. The biopsy device 600 additionally includes hollow needle 612 associated with the distal end 606 of the biopsy device 600. As more clearly illustrated in FIG. 30, the hollow needle 612 defines a channel into which a stylet 614 and associated cutting element 615 are at least partially disposed.

While the triggers 608, 610 are illustrated as being on different ends of the device 600, the triggers 608, 610 are part of the same contiguous trigger and therefore move co-dependently. The triggers 608, 610 are also operably connected to the stylet 614, and when either trigger 608, 610 is activated, the biopsy element 615 of the stylet 614 is exposed and/or extends away from the distal end of the hollow needle 612. The coordinated movement of components within the biopsy device 600 is controlled by a drive mechanism 616, which can include a spring mechanism, among other things.

Figure 29:
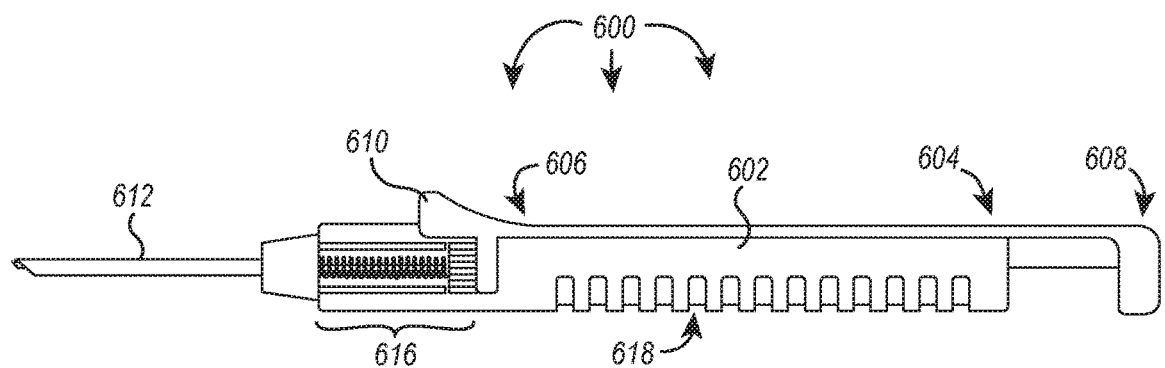
FIG. 29 illustrates another exemplary biopsy device.
Figure 30:
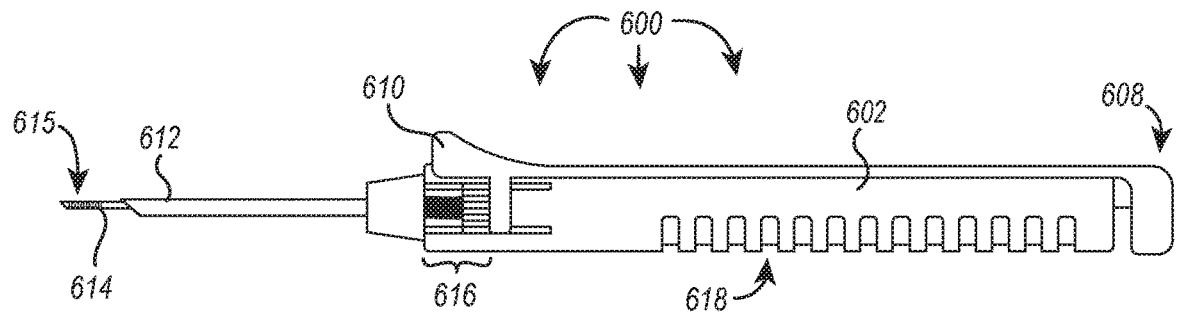
FIG. 30 illustrates the biopsy device of FIG. 29 with the trigger activated.

The biopsy device 600 of FIGS. 29 and 30 can additionally include a plurality of grips 618 to increase the ease of handling the biopsy device 600. It should be appreciated that the biopsy device 600 can additionally, or alternatively, include any of the foregoing components and/or features described herein and may be operable in the same or similar manner.

Biopsy devices of the present disclosure may be single-use or reusable. Accordingly, individual components comprising the disclosed biopsy devices may include one or more materials, which may be chosen based on the potential or desired number of uses. For example, reusable devices may include sterilizable materials, such as metal alloys or autoclave resistant plastics. Exemplary autoclave resistant plastics include polypropylene, polymethylpentene, polycarbonate, and polymethyl methacrylate. In some embodiments, select elements of the biopsy device are made from a metal alloy, such as steel, surgical stainless steel, tungsten carbide, titanium alloys, or similar. For example, the hollow needle, the stylet, and/or the biopsy element may preferably be made from a metal alloy. Components of the biopsy device may additionally be made of a thermoplastic (e.g., polypropylene, polyethylene, polyvinyl chloride, polycarbonate, etc.), elastomer (e.g., polyisoprene, polybutadiene, nitrile rubbers, polycholorprene, etc.), thermoplastic elastomer (e.g., thermoplastic olefins, thermoplastic polyurethanes, etc.), silicone, or similar to enable desired mechanical and/or aesthetic properties.

In some embodiments, the materials comprising the biopsy device (or components thereof) are chosen to be compatible with imaging equipment such as ultrasound, x-ray-based imaging equipment, computed tomography, or magnetic resonance imaging (MRI). For example, for use with ultrasound imaging, the tip of the biopsy device may have an echogenic surface. Or in the instance of use with magnetic resonance imaging (MRI), the entire biopsy device or at least portions may be made of non-ferromagnetic materials, such as MRI-compatible metal alloys or other materials. Additionally, or alternatively, the materials may be chosen to be compatible with endoscopic use. For example, the stylet may be made of a semi flexible material that can be passed through a sheath and/or guide to a distant biopsy site. Accordingly, in some embodiments, the hollow needle may be replaced with a hollow sheath/guide used in endoscopic procedures.

Although particular attention has been paid to the use and application of the foregoing exemplary embodiments with fine needle biopsy, the devices disclosed above with reference to the Figures can, in some embodiments, include needles having a smaller gauge (e.g., 22 G or less, 18 G or less, between 6 G and 22 G, between 6 G and 18 G, between 8 G and 16 G, etc.). For example, biopsy devices disclosed herein can be implemented with a lower gauge hollow needle (with a stylet and cutting tip scaled accordingly) to perform a non-fine needle core biopsy of an organ, such as, for example, a liver. In some embodiments, the same—or similar—foregoing biopsy devices are operable for use retrieving a biopsy from any body site, and the length of the hollow needle (and other relevant features) can be extended or reduced according to the biopsy site or preference of the physician.

In some embodiments, the hollow needle is the biopsy element. For example, the hollow needle may be directly associated with the core body of the disclosed biopsy devices without a stylet associated therewith. Instead of the biopsy element of the stylet performing the biopsy, the hollow needle, itself, performs the biopsy. With such a configuration, the biopsy device can be configured to receive and couple to common, commercially available hollow needles.

In some embodiments, some of the components of the biopsy devices disclosed herein (e.g., the attachment base and the elongated body) are fused or otherwise sealed to prevent tampering of the components. In some embodiments, the components of the biopsy devices can be uncoupled and the inner mechanism opened such that the lumen of the elongated body can be accessed. This provides the advantage of being able to adjust one or more elements of the biopsy device, including, for example, adjusting/replacing the stylet and/or associated biopsy element. For example, the location and/or depth of the biopsy sample to be taken or the physician's preference may guide what type of hollow needle and/or biopsy element to use. Additionally, or alternatively, a biopsy can be taken at a first site, the biopsy device opened and the stylet removed and replaced with a new, sterile stylet (and associated biopsy element), optionally along with a new, sterile hollow needle.

It should be appreciated that while the illustrated embodiments of the Figures depict attachments between various components as interlocking complementary threads (e.g., attachment of second trigger 210 to attachment base 216 via complementary threads 232, 234 and attachment of the attachment base 216 to the elongated body 202 via complementary threads 236, 240), components of the disclosed biopsy devices can alternatively be associated by a compression fitting, a keyseat assembly, or an interference fit.

In some embodiments, the trigger and/or trigger assembly of the disclosed biopsy devices can be associated with a core body and/or stylet in a number of alternative ways. For example, the core body can be associated with the stylet and/or trigger assembly by fitting within a wedged/notched groove. As another example, the stylet can be threadedly attached to the core body and/or the core body can be threadedly attached to the trigger or component of the trigger assembly. As yet another example, the trigger mechanism and core body and/or the core body and the stylet can be attached via a compression fitting, keyseat assembly (with, for example, the key on the stylet and the keyseat on the core body, where the keyseat may additionally include a curved region to lock the key thereat), or by other means.

Moreover, in some embodiments, the spring mechanism can be located in a different position within the biopsy device than where it is illustrated in the Figures. For example, the spring mechanism can be associated with the trigger or trigger assembly and the elongated body such that the base portion of the trigger or a portion of the trigger assembly acts to compress the spring mechanism against a surface of the proximal end of the elongated body.

As described above, often in a needle biopsy, for example in FNA, a negative pressure is created by withdrawing a plunger within a syringe, thus creating a suction effect that draws material, cells, tissue, and/or liquid into the needle. Often, a general-use syringe and needle is used in such a procedure. And for many medical practitioners, such as specialized physicians, this requires the use of both hands, one to hold the syringe and another to slowly and carefully withdraw the plunger from the syringe. But this is problematic, as an imaging device, such as an ultrasound probe is often used while performing the biopsy so as to image and thus properly identify the area to be biopsied. It is preferable to be able to obtain the biopsy with one hand, such as the right hand if the physician is right-handed, and properly place the imaging probe, for example, the ultrasound probe with the left hand. But it can be very difficult to both hold the syringe and withdraw the plunger so as to apply a negative pressure the needle with only one hand, in this example, the right hand.

Accordingly, with this in mind, in another embodiment, the biopsy device according to this disclosure further includes a negative pressure creating mechanism that applies a negative pressure to the distal end of the needle so as to draw the material, tissue, liquid, or cells to be biopsied within the hollow needle. The negative pressure creating mechanism may include a pump mechanism that creates pressure based on the trigger being activated (e.g., depressed) into the elongated body. The negative pressure creating mechanism may include a negative pressure volume chamber, such as a small evacuated chamber, which is slightly opened with a channel that communicates with the hollow needle upon activation of the trigger. Such a negative pressure volume chamber may be arranged within the elongated body. Or, in another embodiment, the negative pressure creating mechanism may be a plunger/syringe-type system within the elongated body. The spring force of the spring mechanism, upon activation of the trigger, can apply a restoring force to the plunger to further push out a plunger from within a syringe chamber thus creating a negative pressure which can be communicated, perhaps by a channel or direct attachment, to the distal end of the hollow needle. Such an arrangement would then create a negative pressure within the hollow needle to draw the tissue, material, liquid, or cells to be biopsied within the hollow needle.

Abbreviated List of Defined Terms

To assist in understanding the scope and content of the foregoing written description and appended claims, a select few terms are defined directly below. Unless defined otherwise, all technical and scientific terms used herein have the same meaning as commonly understood by one of ordinary skill in the art.

As used herein, the term "biopsy" includes tissue removed from a living (or non-living) body to discover the presence, cause, or extent of a disease, dysfunction, or another affliction. A biopsy can additionally include fluids at or near the biopsy site and/or cells that are not part of an ordered (or disordered) tissue. For example, a biopsy taken of a lymph node may contain one or more of the structured tissue of the capsule, lymph fluid, and circulating and/or resident immune cells (e.g., dendritic cells, macrophages, T cells, B cells, plasma cells, etc.). Accordingly, the term "biopsy" is intended to broadly encompass cellular and non-cellular content removed from the body.

The term "fine," as used herein and with reference to a needle or similar percutaneous device, is illustrative of the gauge of the needle. In general, a "fine needle" includes 18-30 G needles. However, a "fine needle" preferably includes 20-28 G needles and more preferably includes 22-27 G needles and most preferably includes 24-25 G needles. The gauge associated with a "fine needle" can be selected in a context-dependent manner and may be selected from by a licensed medical professional performing a biopsy for any or no reason at all. For example, a higher gauge needle may be used when performing a biopsy on a small, targeted area or on a delicate organ/tissue where use of a lower gauge needle may cause unwarranted damage to surrounding tissue. In some embodiments, the gauge of needle is selected by a physician based on availability or preference.

The term "patient" generally refers to any animal, for example a mammal, under the care of a physician, as that term is defined herein, with particular reference to humans under the care of an endocrinologist, oncologist, surgeon, primary care physician or other relevant medical professional that performs biopsies. For the purpose of the present application, a "patient" may be interchangeable with an "individual." In some embodiments, the individual is a human patient.

The term "physician" as used herein generally refers to a medical doctor, and particularly a specialized medical doctor, such as an endocrinologist, oncologist, surgeon, primary care physician, radiologist, or other specialized medical doctor performing biopsies. This term may, when contextually appropriate, include any other medical professional, including any licensed medical professional or other healthcare provider, such as a physician's assistant, a nurse, a veterinarian (such as, for example, when the patient is a non-human animal), etc.

As used herein, the term "spring mechanism" includes any elastic object that can store mechanical energy. In some embodiments, a spring mechanism is a helical metal coil that, when compressed, builds up an axial force that causes the spring to rebound when the force is relieved. A "spring mechanism," as used herein, is also intended to include other elastic objects such as a gas and/or fluid filled elastic bag that is compressible such that, when compressed, the gas and/or fluid is similarly compressed, providing resistance and/or an opposing force as the pressure of the gas and/or fluid filled elastic bag increases due to the reduction in volume. Other similar elastic objects operable to store mechanical energy are included within the scope of the term "spring mechanism."

As used herein, directional terms, such as "top," "bottom," "left," "right," "up," "down," "upper," "lower," "proximal," "distal," "adjacent," and the like are used herein solely to indicate relative directions and are not otherwise intended to limit the scope of the disclosure and/or claims.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the disclosure or claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

The present disclosure may be embodied in other specific forms without departing from its spirit or essential characteristics. The described embodiments are to be considered in all respects only as illustrative and not restrictive. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes that come within the meaning and range of equivalency of the claims are to be embraced within their scope.

What is claimed is:

1. A biopsy device comprising:
    an elongated body having a distal end and a proximal end;
    an attachment base secured to the distal end of the elongated body and having an aperture formed therethrough;
    a hollow needle coupled to the attachment base, the hollow needle defining a continuous channel extending from the aperture of the attachment base and along a length of the hollow needle;
    a first trigger associated with the proximal end of the elongated body;
    a second trigger associated with the distal end of the elongated body;
    a stylet disposed within the channel and operably connected to the first trigger and the second trigger, the stylet including a biopsy element, the biopsy element being configured to extend beyond the distal end of the hollow needle in response to operation of either the first trigger or the second trigger in a first direction, the biopsy element being configured to subsequently retract within the channel of the hollow needle in response to operation of either the first trigger or the second trigger in a second direction;
    a spring mechanism disposed within a lumen defined by the elongated body and operably connected to the first trigger and the second trigger, the spring mechanism configured to compress in response to operation of either the first trigger or the second trigger in the first direction, extending the biopsy element beyond the distal end of the hollow needle, and to rebound following compression and in response to operation of either the first trigger or the second trigger in the second direction, the rebound causing the biopsy element to retract toward or within the channel; and
    a rotation mechanism operably connected to the first trigger and the second trigger, the rotation mechanism being configured to rotate the biopsy element in response to operation of the first trigger or the second trigger such that the biopsy element both (i) rotates and (ii) extends or retracts relative to the distal end of the hollow needle,
    wherein the stylet moves co-dependently with the first trigger and the second trigger, and wherein the first trigger and the second trigger are operably connected to one another by a core body such that:
        movement of the first trigger in the first direction causes movement of the second trigger in the first direction,
        movement of the first trigger in the second direction causes movement of the second trigger in the second direction,
        movement of the second trigger in the first direction causes movement of the first trigger in the first direction, and
        movement of the second trigger in the second direction causes movement of the first trigger in the second direction.

2. The biopsy device of claim 1, wherein the core body is coupled to the stylet at a first end and disposed within the lumen between the first trigger and the second trigger, the core body including a stopper configured to interact with and compress the spring mechanism when either the first trigger or the second trigger is operated.

3. The biopsy device of claim 2, further comprising a retractable cover, the retractable cover being slidably associated along the attachment base and defining an aperture having a larger diameter than a diameter of the hollow needle.

4. The biopsy device of claim 3, wherein the hollow needle comprises a metallic, hollow fine needle within a range of 20-27 G.

5. The biopsy device of claim 1, wherein the first trigger includes a concave surface.

6. The biopsy device of claim 1, wherein the second trigger is shaped such that a first end of the second trigger comprises a smaller diameter than a respective second end.

7. The biopsy device of claim 1, wherein the biopsy element comprises a spiral tip biopsy element, an alligator biopsy element, a second hollow needle, or a core biopsy needle.

8. The biopsy device of claim 1, wherein the biopsy element includes an expanded spiral tip having a low friction surface configured to reduce an amount of energy necessary to transit a biopsy from a distal portion of the expanded spiral tip to or along a proximal portion of the expanded spiral tip.

9. The biopsy device of claim 1, further comprising a retractable cover associated with the elongated body, the retractable cover configured to occlude a distal tip of the hollow needle in a first position and to expose the distal tip of the hollow needle in a second position.

10. The biopsy device of claim 9, wherein the retractable cover defines an aperture having a larger diameter than the diameter of the hollow needle, and wherein the retractable cover is positioned to slidably transition between the first position and the second position such that the distal tip of the hollow needle traverses the aperture when transitioning between the first position and the second position.

11. The biopsy device of claim 1, wherein the biopsy element comprises a metallic, hollow fine needle within a range of 24-32 G.

12. The biopsy device of claim 1, wherein the first trigger comprises a locking mechanism.

13. The biopsy device of claim 12, wherein the locking mechanism is configured to engage, thereby retaining the spring mechanism in a compressed configuration, upon a first trigger pressure threshold being exceeded.

14. A method of obtaining a biopsy sample with a single stick, comprising:
   inserting the hollow needle of the biopsy device of claim 1 into a biopsy site; and
   obtaining a biopsy sample by reiteratively compressing and rebounding either the first trigger or the second trigger, respectively extending and retracting the biopsy element beyond the distal end of the hollow needle.

15. The biopsy device of claim 1, wherein the biopsy element comprises an 18-30 G needle.

* * * * *